US012685834B2

(12) United States Patent
Hocking et al.

(10) Patent No.: US 12,685,834 B2
(45) Date of Patent: Jul. 21, 2026

(54) RESPIRATORY INTERFACE

(71) Applicant: Fisher & Paykel Healthcare Limited, Auckland (NZ)

(72) Inventors: Jake Baker Hocking, Auckland (NZ); Mark Arvind Mclaren, Auckland (NZ); Tony William Spear, Auckland (NZ); Melissa Catherine Bornholdt, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 543 days.

(21) Appl. No.: 16/310,978

(22) PCT Filed: Jul. 6, 2017

(86) PCT No.: PCT/IB2017/054060
§ 371 (c)(1),
(2) Date: Dec. 18, 2018

(87) PCT Pub. No.: WO2018/007966
PCT Pub. Date: Jan. 11, 2018

(65) Prior Publication Data
US 2019/0175863 A1 Jun. 13, 2019

Related U.S. Application Data

(60) Provisional application No. 62/438,207, filed on Dec. 22, 2016, provisional application No. 62/412,399, (Continued)

(51) Int. Cl.
| A61M 16/08 | (2006.01) |
| A61M 16/04 | (2006.01) |
| A61M 16/06 | (2006.01) |

(52) U.S. Cl.
CPC .... *A61M 16/0816* (2013.01); *A61M 16/0493* (2014.02); *A61M 16/0611* (2014.02); (Continued)

(58) Field of Classification Search
CPC .......... A61M 16/0816; A61M 16/0611; A61M 16/0666; A61M 16/0683; A61M 16/0875; (Continued)

(56) References Cited

U.S. PATENT DOCUMENTS

| 3,181,895 A | * | 5/1965 | Cator | ..................... F16L 37/004 |
| | | | | 285/1 |
| 3,582,017 A | * | 6/1971 | Zecca | .................... B64G 1/645 |
| | | | | 102/377 |

(Continued)

FOREIGN PATENT DOCUMENTS

| EP | 3471811 B1 | 12/2017 |
| WO | WO 2011/059346 A1 | 5/2011 |

(Continued)

OTHER PUBLICATIONS

Hopcroft, Matthew; Nix, William; Kenny, Thomas; "What is the Young's Modulus of Silicon?," Journal of Microelectromechanical Sytems, vol. 19, No. 2, Apr. 2010. (Year: 2010).*

(Continued)

*Primary Examiner* — Rachel T Sippel
*Assistant Examiner* — Jacqueline M Pinderski
(74) *Attorney, Agent, or Firm* — VIA LLP

(57) ABSTRACT

Respiratory interfaces have magnetic elements for coupling and/or adjusting parts of the interface, such as a magnetic coupling system (121*a,* 121*b*) arranged to magnetically couple a seal module (101) to a mask frame (100), or to magnetically hold a seal adjustment position. A magnet or magnets may have an embedded particulate magnetic material.

23 Claims, 23 Drawing Sheets

Related U.S. Application Data filed on Oct. 25, 2016, provisional application No. 62/358,731, filed on Jul. 6, 2016.

(52) U.S. Cl.
CPC .... *A61M 16/0616* (2014.02); *A61M 16/0666* (2013.01); *A61M 16/0683* (2013.01); *A61M 16/0875* (2013.01); *A61M 16/0825* (2014.02); *A61M 2205/0272* (2013.01); *A61M 2205/12* (2013.01); *A61M 2205/43* (2013.01); *A61M 2205/581* (2013.01)

(58) Field of Classification Search
CPC .......... A61M 16/0493; A61M 16/0616; A61M 16/0825; A61M 2205/0272; A61M 2205/12; A61M 2205/43; A61M 2205/581
USPC .................................................. 128/202.27
See application file for complete search history.

(56) References Cited

U.S. PATENT DOCUMENTS

| | | | | | |
|---|---|---|---|---|---|
| 5,096,230 | A | * | 3/1992 | Pausch | F16L 37/004 285/9.1 |
| 6,668,828 | B1 | * | 12/2003 | Figley | A61M 16/0051 128/204.22 |
| 6,805,117 | B1 | * | 10/2004 | Ho | A61M 16/0683 128/207.17 |
| 7,793,987 | B1 | * | 9/2010 | Busch | A61M 16/161 285/9.1 |
| 11,419,999 | B2 | | 8/2022 | Patel | |
| 2005/0155604 | A1 | | 7/2005 | Ging et al. | |
| 2007/0184674 | A1 | * | 8/2007 | Koch | H01H 51/2209 439/39 |
| 2008/0264413 | A1 | * | 10/2008 | Doherty | A61M 39/1011 128/202.27 |
| 2009/0101141 | A1 | * | 4/2009 | Ging | A62B 18/084 128/201.22 |
| 2010/0000534 | A1 | * | 1/2010 | Kooij | A61M 16/0616 128/204.18 |
| 2011/0000492 | A1 | * | 1/2011 | Veliss | A61M 16/0666 128/207.13 |
| 2011/0084474 | A1 | * | 4/2011 | Paden | F16L 37/004 285/9.1 |
| 2013/0263858 | A1 | * | 10/2013 | Ho | A61M 16/0683 128/205.25 |
| 2013/0276923 | A1 | * | 10/2013 | Wolff | F16L 37/32 285/1 |
| 2013/0303000 | A1 | * | 11/2013 | Witter | F16L 37/004 403/324 |
| 2014/0077044 | A1 | * | 3/2014 | Witter | H01F 7/0263 403/324 |
| 2014/0283826 | A1 | * | 9/2014 | Murray | A61M 16/0683 128/202.27 |
| 2014/0360503 | A1 | * | 12/2014 | Franklin | A61M 16/0683 128/205.25 |
| 2015/0055279 | A1 | * | 2/2015 | McBroom | F16B 35/06 361/679.01 |
| 2015/0174354 | A1 | * | 6/2015 | Matula, Jr. | A61M 16/0683 128/202.27 |
| 2015/0250972 | A1 | | 9/2015 | Haibach et al. | |
| 2015/0283349 | A1 | | 10/2015 | McLaren et al. | |
| 2015/0335846 | A1 | * | 11/2015 | Romagnoli | A61M 16/0057 128/201.13 |
| 2015/0343582 | A1 | * | 12/2015 | Ebihara | B23B 31/28 279/128 |
| 2015/0352308 | A1 | * | 12/2015 | Cullen | A61M 16/0683 128/205.25 |
| 2016/0263339 | A1 | * | 9/2016 | Greenberg | A61M 16/06 |
| 2017/0333660 | A1 | * | 11/2017 | Haibach | A61M 16/0683 |
| 2018/0140796 | A1 | * | 5/2018 | Haibach | A61M 16/0683 |
| 2018/0200468 | A1 | * | 7/2018 | Chodkowski | A61M 16/0605 |
| 2018/0318539 | A1 | * | 11/2018 | Scheiner | A61M 16/0683 |
| 2019/0125998 | A1 | * | 5/2019 | Baiko | A61M 16/0666 |

FOREIGN PATENT DOCUMENTS

| | | |
|---|---|---|
| WO | WO 2014/045245 A1 | 3/2014 |
| WO | WO 2014/110622 A1 | 7/2014 |

OTHER PUBLICATIONS

The CPAP Shop, "Respironics Amara Full Face CPAP Mask Review", Published Jul. 11, 2012 on Youtube [online], Retrieved on Nov. 8, 2024 from: https://www.youtube.com/watch?v=hx8GwD4MHAE (Year: 2012).*

International Search Report; PCT/IB2017/054060; dated Oct. 9, 2017; 14 pages.

European Extended Search Report, re Application No. 17823742.6, dated Mar. 2, 2020; 6 pages.

* cited by examiner

112

113

110

100

108

109

102

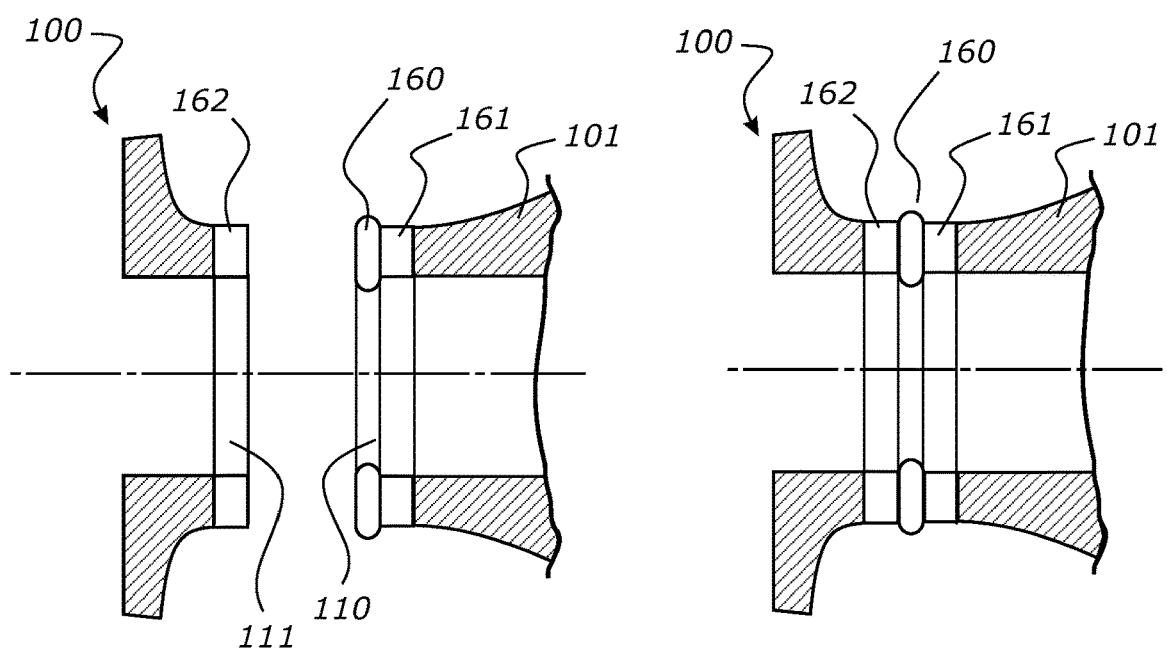
FIGURE 5A                    FIGURE 5B
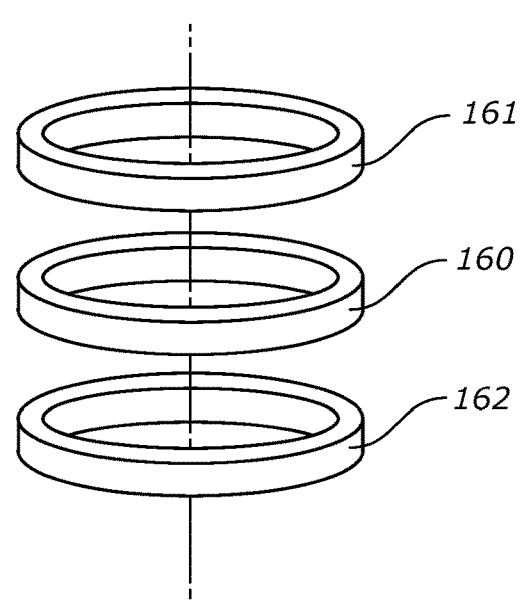
FIGURE 5C

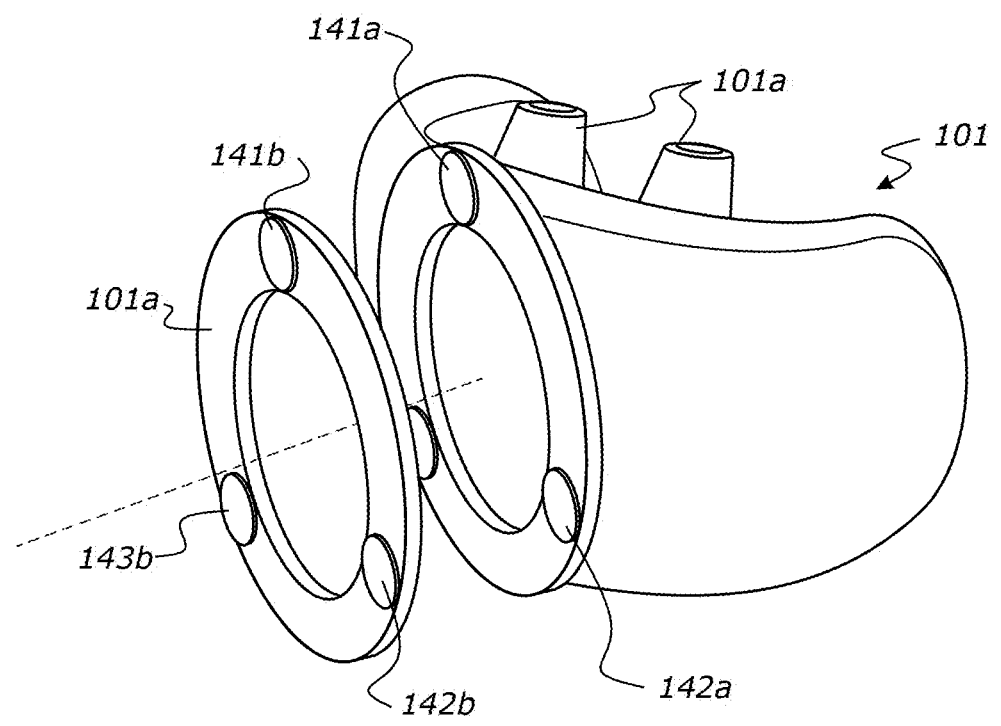
FIGURE 7A
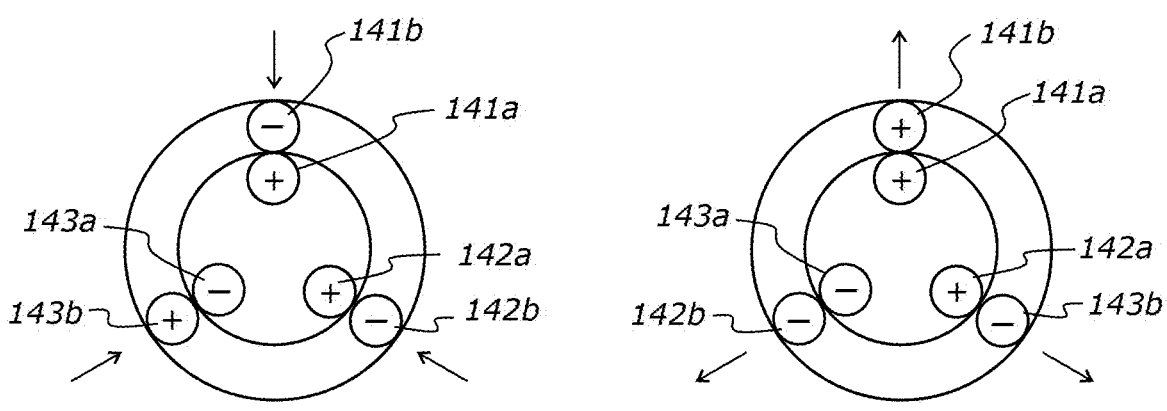
FIGURE 7B                    FIGURE 7C

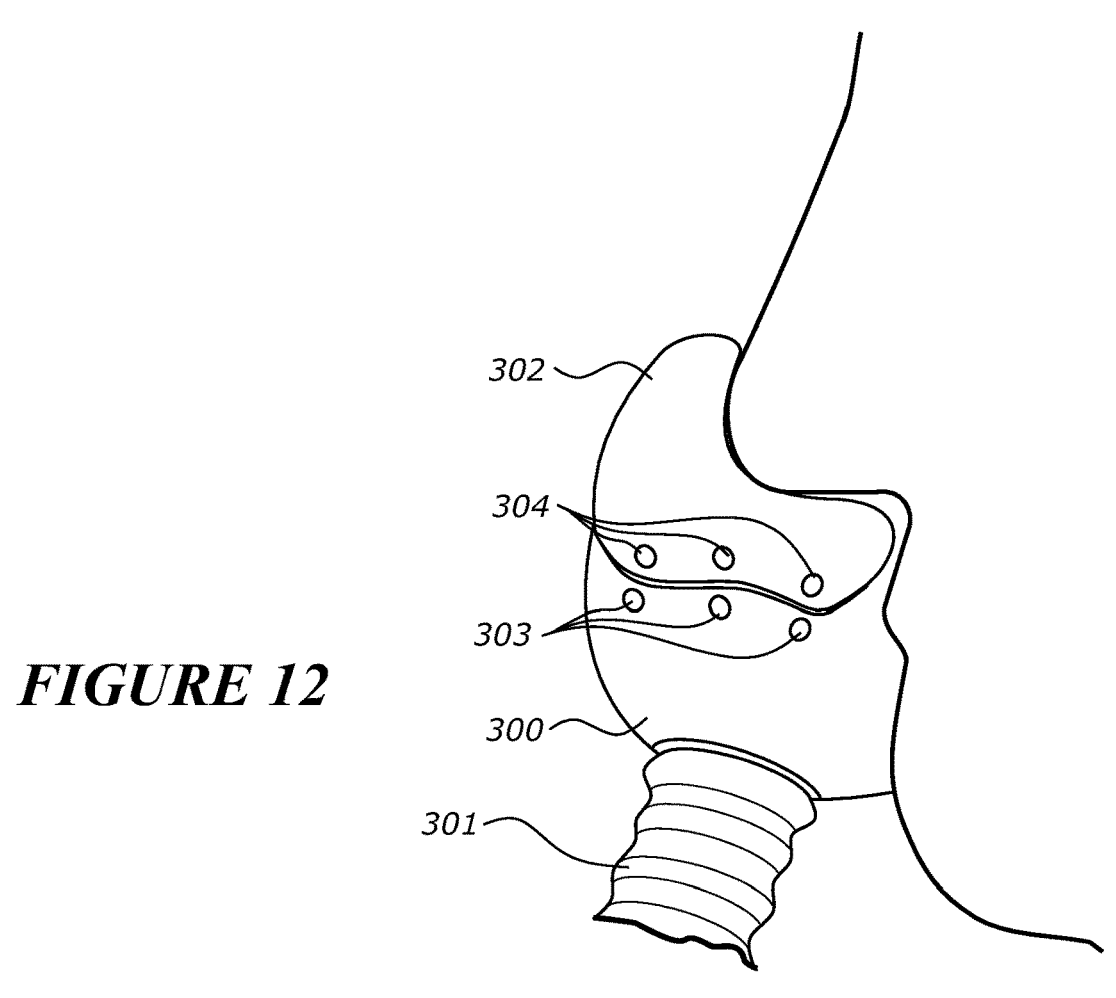
*FIGURE 12*
*FIGURE 13*
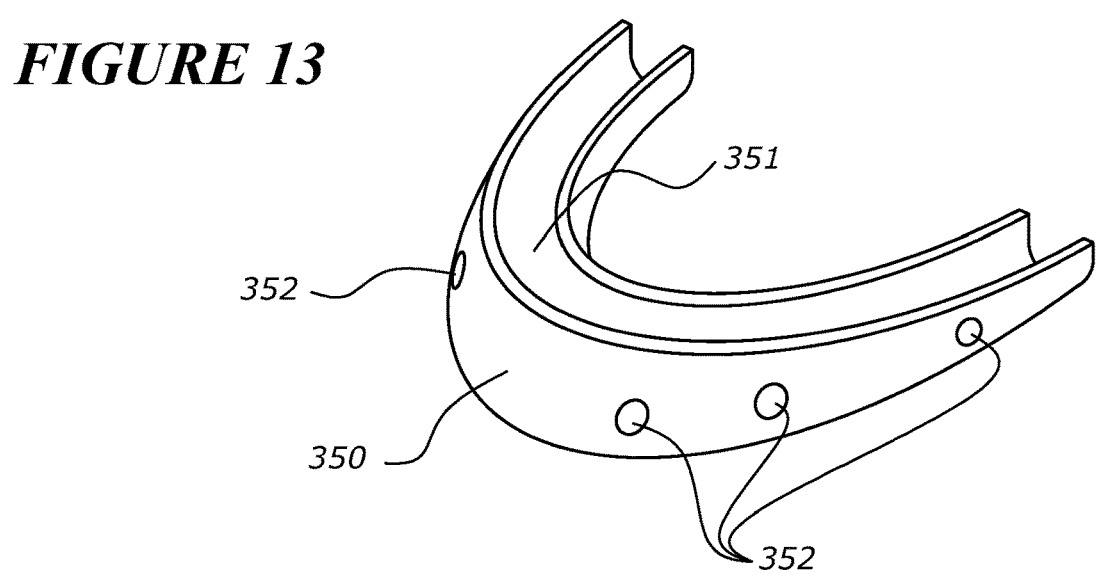

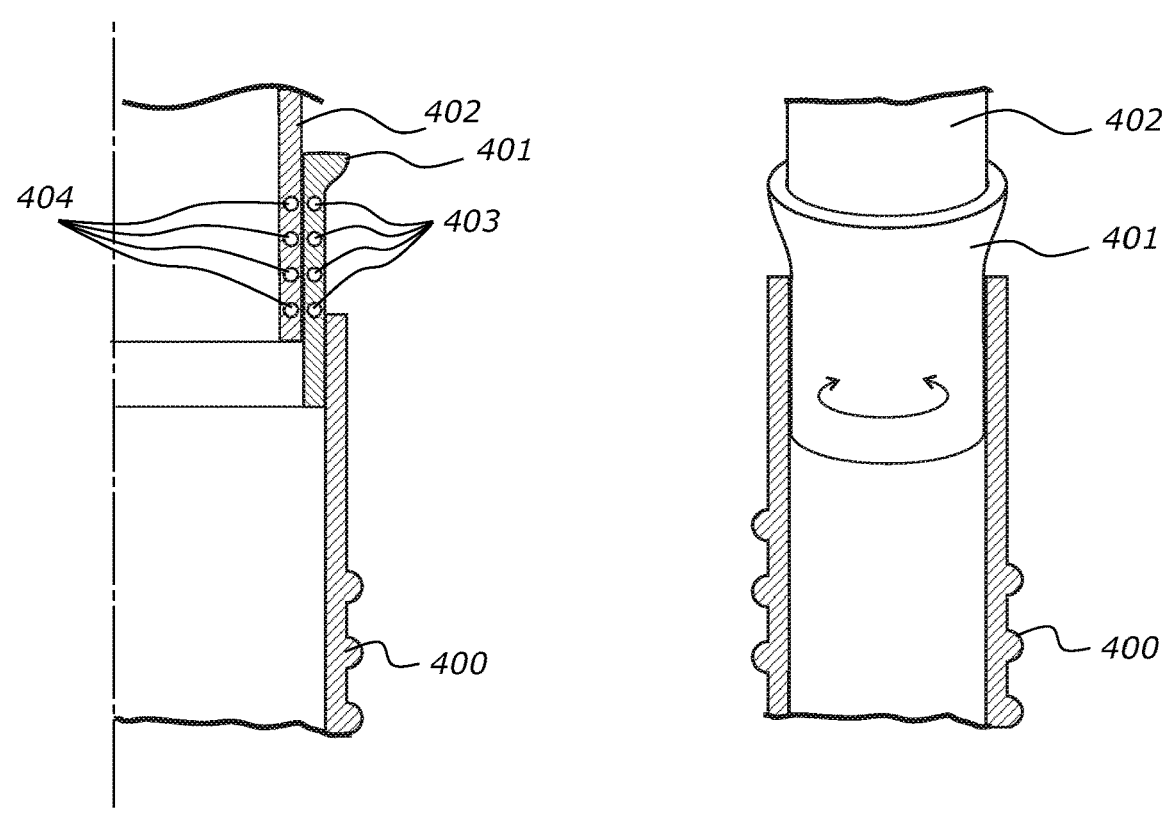
FIGURE 14A                    FIGURE 14B
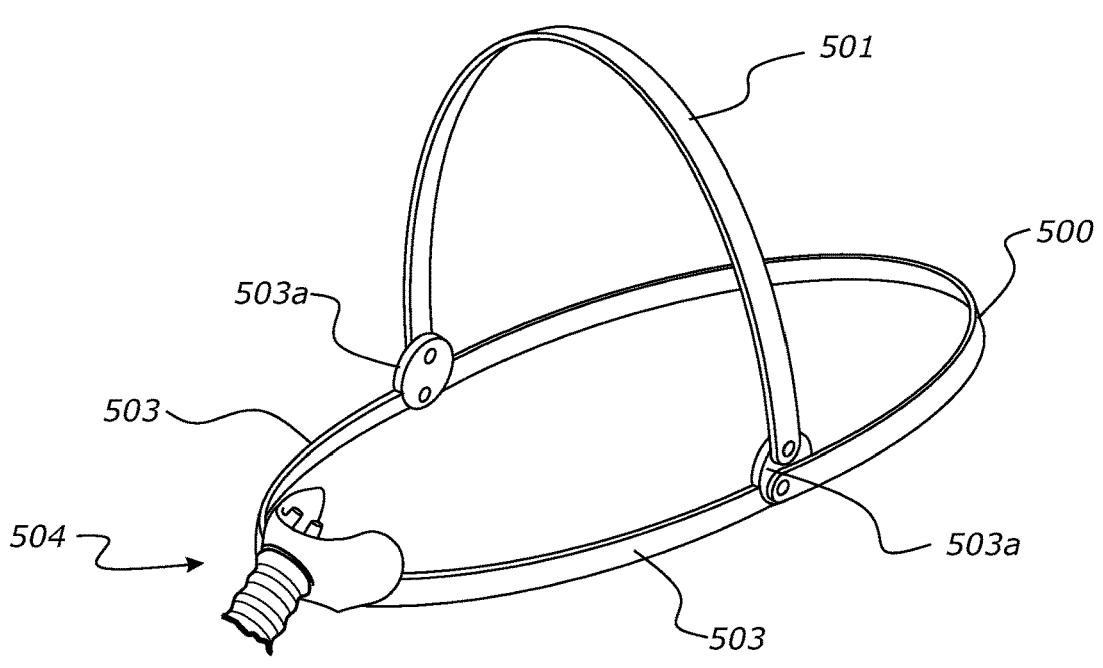
FIGURE 15

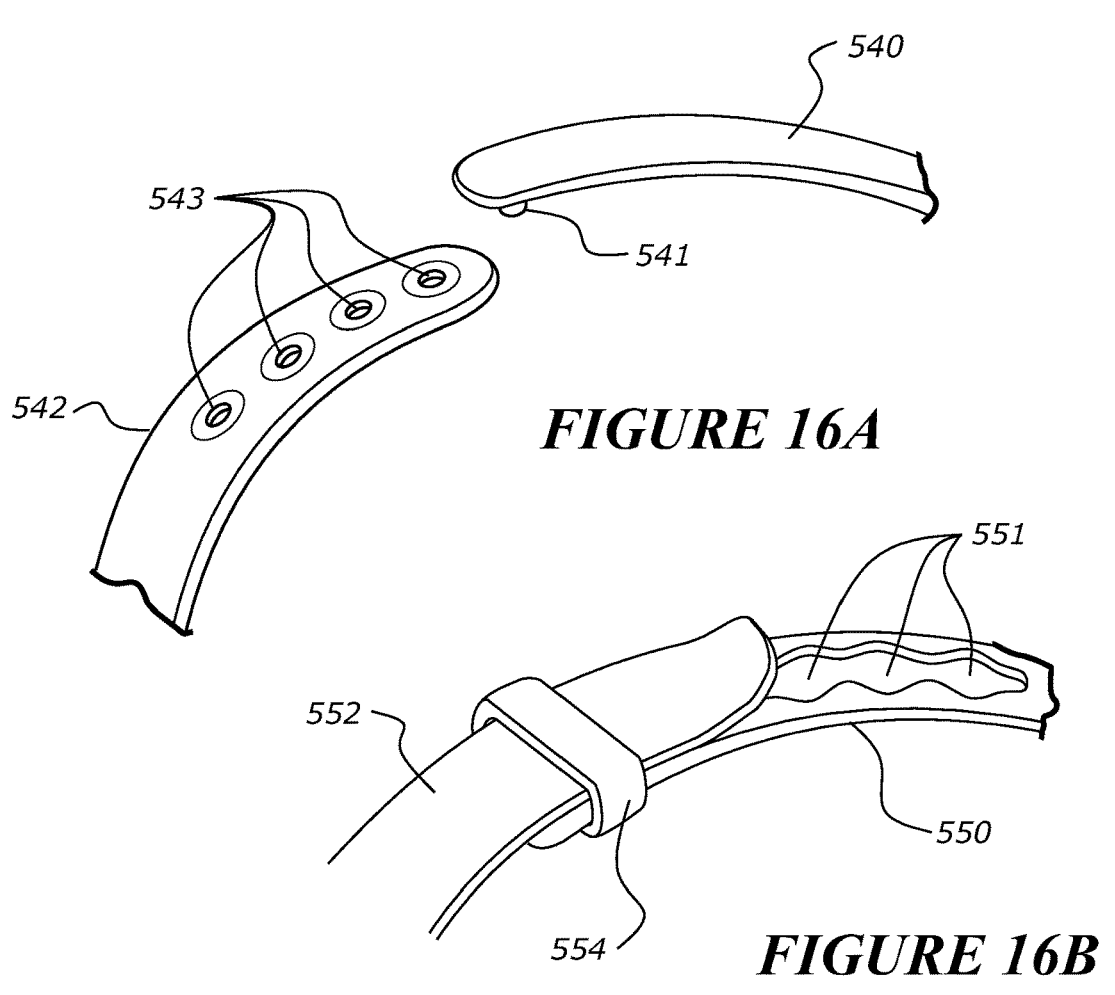
*FIGURE 16A*
*FIGURE 16B*
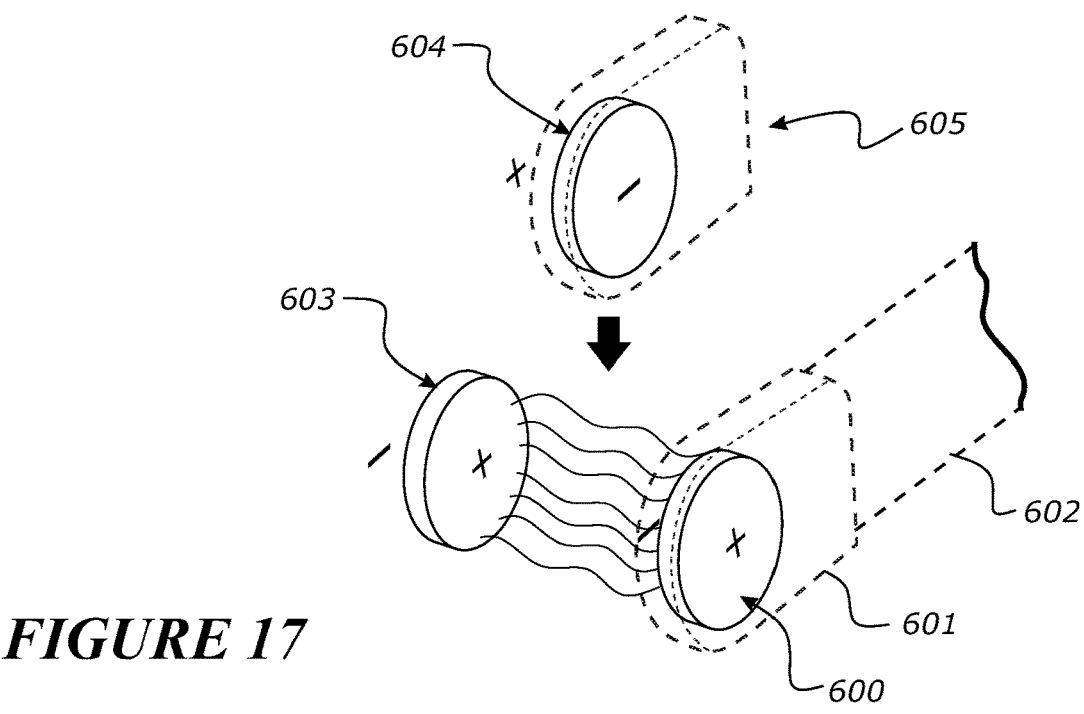
*FIGURE 17*

701

703

701

703

701

703

N    S    ⟷    S    N

705

705

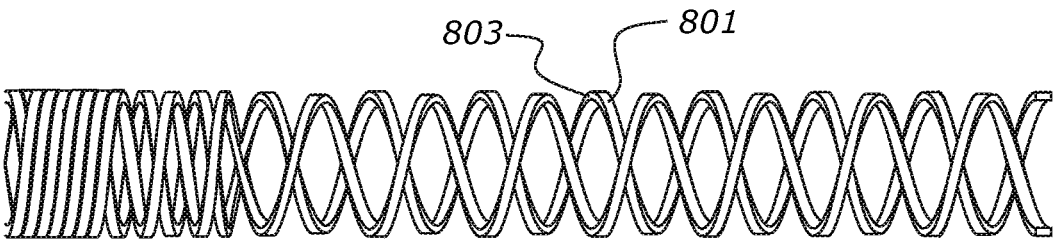
FIGURE 23
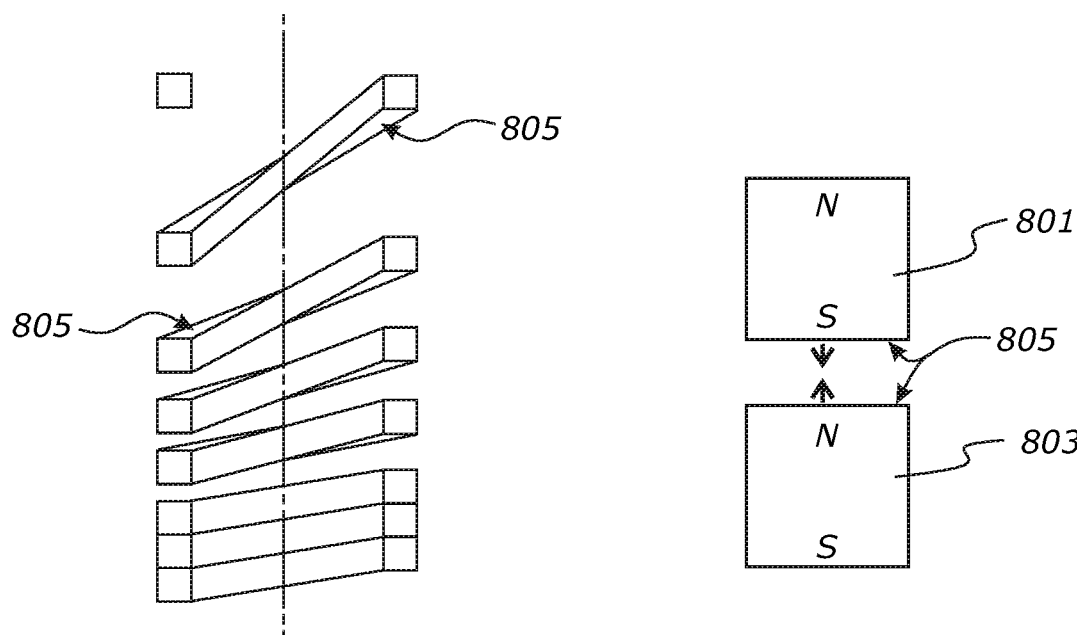
FIGURE 24          FIGURE 25
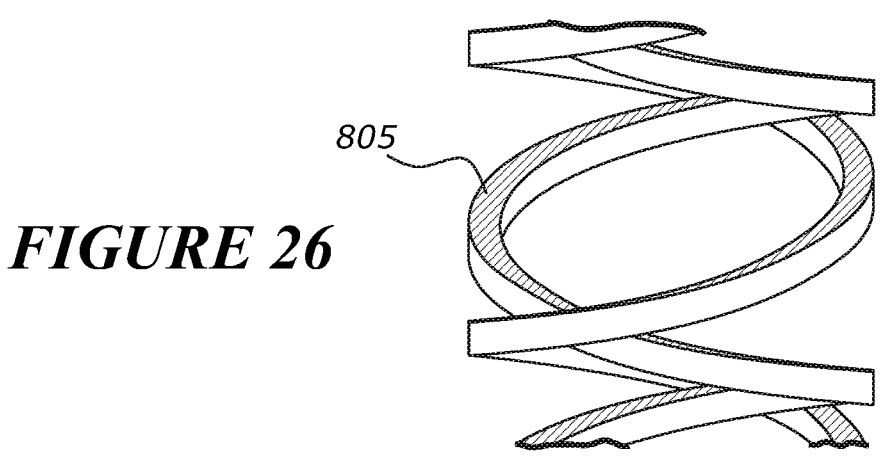
FIGURE 26

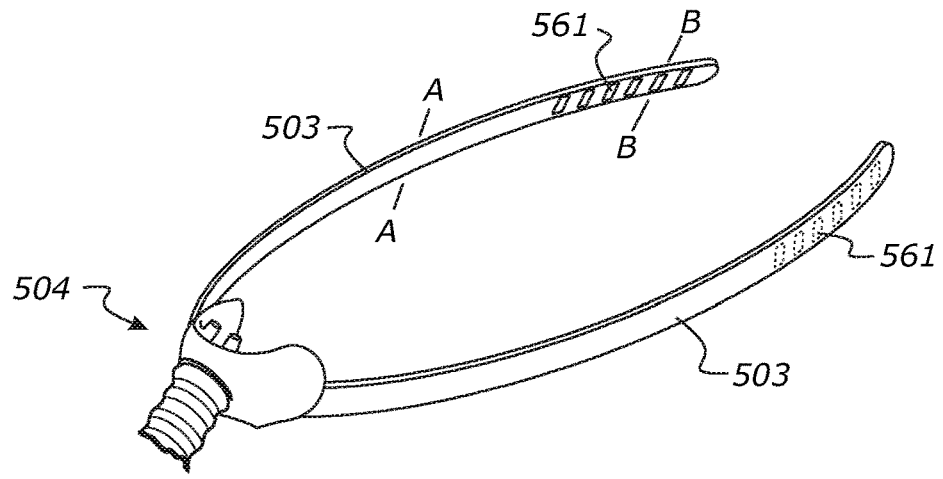
FIGURE 27
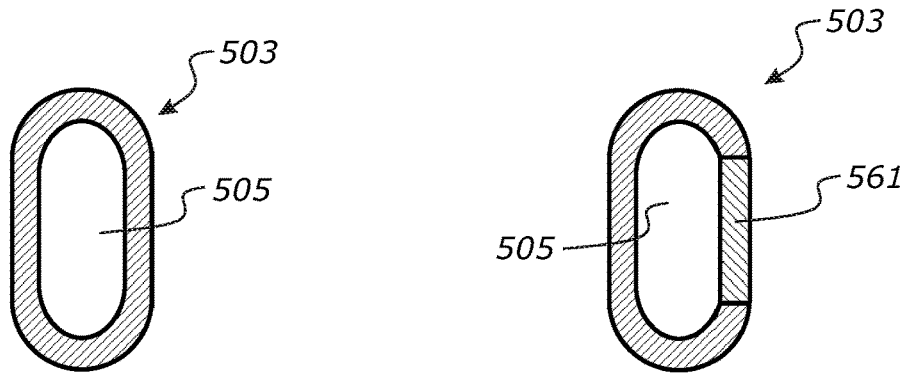
FIGURE 28a         FIGURE 28b
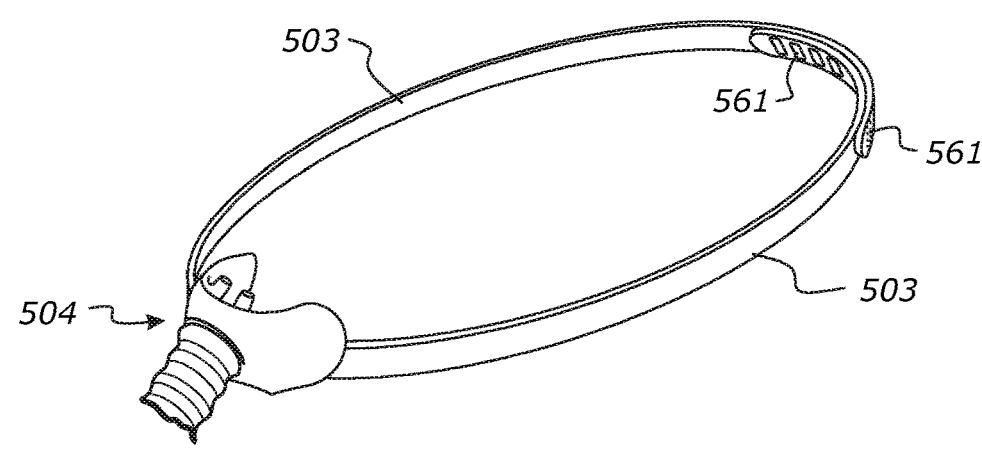
FIGURE 29

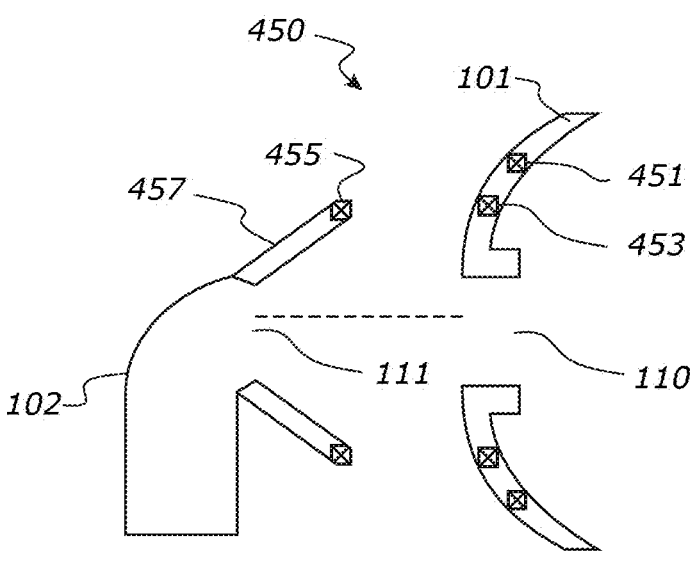
FIGURE 37
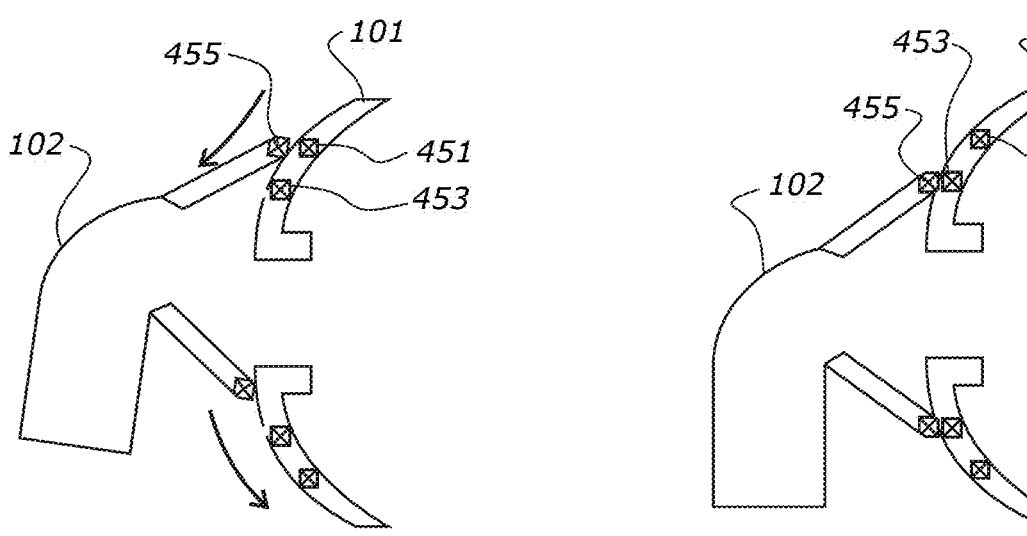
FIGURE 38a          FIGURE 38b

RESPIRATORY INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention generally relates to respiratory interfaces and in particular but not exclusively to respiratory interfaces comprising magnetic elements for coupling and/or adjusting parts of the interface.

Description of the Related Art

Respiratory interfaces or masks are used to provide respiratory gas or gases, such as air in CPAP therapy, including in for example VPAP and BiPAP systems, or NIV, or high flow rate therapy, for example.

Commonly a respiratory interface comprises a mask frame to which for example headgear attaches which holds the interface in position on the user's head when worn, and a seal module (sometimes also referred to as a cushion or cushion module) configured to couple to the mask frame and interface to a user's mouth and/or nose to deliver respiratory gases to the user. A respiratory interface may comprise a nasal, oral, or oro-nasal (also referred to as full face) seal module. In turn an interface may be an indirect interface which covers the nose, mouth, or both, or a direct interface such as an interface comprising nasal nozzles or pillows or similar which enter into and seal against or within the nares of the wearer or cannula which non-sealingly enter the nares. The seal module can be formed entirely or almost entirely of a soft material which is comfortable against the wearer's face, such as commonly a silicone material, or the seal module may comprise a rigid or semi-rigid frame interfacing part formed of a rigid or semi-rigid material and which couples to the mask frame and a seal part formed of a relatively soft material.

Typically the seal module couples mechanically to the mask frame via a friction fit, snap fit, or other interference fit, of formations on the seal module and mask frame to one another. The seal module couples detachably to the mask frame so that it can be removed for cleaning or so that different sizes of seal module may interface with the mask frame.

SUMMARY OF THE INVENTION

It is an object of the present disclosure to provide one or more constructions and/or methods that will at least go some way towards improving on the above or that will at least provide the public or the medical profession with a useful choice.

Seal Module to Frame Magnetic Connection

In broad terms in one aspect the invention comprises a respiratory interface comprising:

a mask frame, a seal module configured to couple to the mask frame and interface to a user's mouth and/or nose to deliver respiratory gases to the user, and a magnetic coupling system arranged to magnetically couple the seal module to the mask frame. Magnetic coupling between a rear, user facing, side of the mask frame and a forward side of the seal module potentially enables a method of use where the seal module can be removed while headgear remains in place on the user. Preferably the magnetic coupling system comprises multiple magnets associated with each of the seal module or mask frame. Preferably, magnets are provided to the seal module and mask frame such that they attract only when the seal module is coupled to the mask frame in a predetermined orientation of the seal module relative to the mask frame and repel when the seal module is offered to the mask frame in any orientation other than said predetermined orientation. Multiple magnets may each comprise a segment of solid (non-particulate) magnetic material or the magnet or magnets comprise particulate magnetic material. In one form the particulate magnetic is material embedded in soft material of the seal module.

In broad terms in another aspect the invention comprises a seal module for a respiratory interface, the seal module configured to couple to a mask frame and interface to a user's mouth and/or nose to deliver respiratory gases to the user, and comprising at least one magnet or ferrous part associated with the seal module to magnetically couple the seal module to the mask frame.

In one form the respiratory interface may include magnets associated with the seal module provided at left and right sides of the seal module and magnets associated with the mask frame are provided at left and right sides of the mask frame. Preferably, magnets associated with the seal module or mask frame are provided to the seal module or mask frame with movement in a direction in which the seal module and mask frame interface so that on offering together the seal module and mask frame magnets associated with the seal module or mask frame move toward the magnets associated with the mask frame or seal module. Preferably the seal module is formed of a soft material. The seal module may comprise a frame interfacing part formed of a rigid or semi-rigid material and which couples to the mask frame and a seal part formed of a relatively soft material. The seal module may be an indirect or direct nasal seal module or an oro-nasal seal module.

Magnetic Hold of Nasal Bridge Compliance Adjustment

In broad terms in another aspect the invention comprises a seal for a respiratory interface, the seal module configured to interface to a user's mouth and/or nose to deliver respiratory gases to the user, and comprising at least one magnet or ferrous part associated with the seal to magnetically hold a first part of the seal in position relative to another part of the seal or a part of a frame of the respiratory interface. Preferably multiple magnets or ferrous parts associated with the seal or a frame to magnetically hold a first part of the seal in multiple selectable adjustment positions of the first part of the seal relative to another part of the seal or a part of a frame of the respiratory interface. Preferably, the seal comprises a frame interfacing part formed of a rigid or semi-rigid material and which couples to a mask frame and a seal part formed of a relatively soft material. In one form the magnet or magnets comprise particulate magnetic material, that is preferably embedded in soft material of the seal module.

In broad terms in another aspect the invention comprises a respiratory interface comprising a mask frame and a seal as above.

Embedded Particulate Magnetic Material

In broad terms in another aspect the invention comprises a respiratory interface and/or headgear, comprising a first part and a second part which in use are coupled together, wherein at least one of the first part and second part comprise a magnet or magnets for magnetic coupling of the first part and second part together which comprise a particulate magnetic material embedded in the first part and/or second part. In one form the particulate magnetic material is embedded in the first part and/or second part by moulding. Preferably, one of the first part and second part is a seal module and the particulate magnetic material is embedded in soft material of the seal module.

Nasal to Full Face Magnetically Connected Seal

In broad terms in another aspect the invention comprises a respiratory interface comprising: a first seal part configured to interface to one of a user's mouth and nose to deliver respiratory gases to the user, and a second seal part configured to interface to the other of a user's mouth and nose to also deliver respiratory gases to the user, and a magnetic coupling system arranged to magnetically couple the first and second seal parts to one another or to a common mask frame and so that at least one of the first and second seal parts is detachable from the other or from common mask frame.

Preferably, at least one magnet associated with one of the first or second seal parts or the mask frame and at least one magnet associated with another of the first or second seal parts or the mask frame are provided to the seal parts or mask frame such that they attract when the seal parts are coupled to each other or to the mask frame in a predetermined correct orientation and repel in any orientation other than said predetermined correct orientation.

Magnet Mouth Connection

In broad terms in another aspect the invention comprises a respiratory interface comprising:

a mask configured to interface to a user's mouth and/or nose to deliver respiratory gases to the user, an oral insert configured to be retained in the user's mouth when the mask is worn, and a magnetic coupling system arranged to magnetically couple the mask frame and oral insert to at least assist in retaining the mask in position on the face of the user. In one form the oral insert is configured to be retained at least in part on upper teeth of the user when worn in the user's mouth. Preferably, the respiratory interface does not also comprise headgear to assist in retaining the mask in position when worn by the user.

Magnetic Conduit Connection

In broad terms in another aspect the invention comprises a respiratory interface comprising:

a mask, a conduit connectable to the mask or to a lead in tube to the mask to deliver respiratory gases to the user, and a magnetic coupling system comprised of magnets associated with both of the conduit to the mask and the mask or a lead in tube to the mask, to magnetically couple the conduit to the mask or a lead in tube to the mask, wherein at least one magnet associated with one of the conduit to the mask and the mask or a lead in tube to the mask and at least one magnet associated with another of the conduit to the mask and the mask or a lead in tube to the mask are provided to the conduit and the mask or a lead in tube to the mask such that they attract when the conduit and the mask or a lead in tube to the mask are coupled to each other or to the mask frame in a predetermined correct orientation and repel in an orientation other than said predetermined correct orientation.

In broad terms in another aspect the invention comprises a magnetic coupling system arranged to magnetically couple a conduit to a fitting or another conduit, comprising a first annular part configured to receive a second annular part over the first annular part, comprising:

at least one magnet associated with one of the first annular part and second annular part and at least one ferrous part associated with another of the first annular part and second annular part, or magnets associated with both of the first annular part and second annular part.

Magnetic Modular Headgear

In broad terms in another aspect the invention comprises headgear for a respiratory interface, comprising:

a first headgear part at least a second headgear part, and a magnetic coupling system arranged to magnetically couple the first and second headgear parts to one another. In one form there may also be a third headgear part and wherein the magnetic coupling system is arranged to magnetically couple the first, second, and third headgear parts to one another. In a further form there may be a fourth headgear part and wherein the magnetic coupling system is arranged to magnetically couple the first, second, third, and fourth headgear parts to one another. Preferably, the first and second, and optionally third or third and fourth headgear parts, comprise at least one magnet at or towards two ends thereof. Alternatively, the first and second, and optionally third or third and fourth headgear parts, comprise at least one magnet at or towards one end thereof and at least one ferrous part at or towards another end thereof. In a further form at least two magnets associated with one with one of one of the first and second, and optionally third or third and fourth headgear parts and another with another of the first and second, and optionally third or third and fourth headgear parts, are provided to the headgear parts such that they attract when the headgear parts are coupled in a predetermined correct orientation and repel in an orientation other than said predetermined correct orientation.

Headgear Buckle (Also Headgear to Mask Buckle)

In broad terms in another aspect the invention comprises a headgear for a respiratory interface, or headgear and a respiratory interface together, comprising:

a first headgear part having one of a protrusion and one or more recesses at or towards an end thereof, a second headgear part having another of a protrusion and one or more recesses at or towards an end thereof, or a mask comprising one of a protrusion and one or more recesses on a part of the mask, a magnetic coupling system arranged to magnetically hold together when engaged to couple same to one another, the protrusion or one or more recesses of the first headgear part and the protrusion or one or more recesses of the second headgear part or mask.

Headgear Connection Broken by 3rd Magnet/Decoupling Mechanism

In broad terms in another aspect the invention comprises headgear for a respiratory interface, or headgear and a respiratory interface together, comprising: a first headgear part comprising a first magnet at or towards an end thereof, a second headgear part comprising a second magnet at or towards an end thereof, or a mask comprising a second magnet on a part of the mask, arranged to magnetically couple the first headgear part to the second headgear part or mask, and a decoupling tool comprising a third magnet and insertable between the first and second magnets when the first headgear part and the second headgear part or mask are coupled, to at least assist in de-coupling same.

In a further form headgear for a respiratory interface may be provided, or headgear and a respiratory interface together, comprising: a first headgear part having an inflatable portion, a second headgear part, a magnetic coupling system arranged to magnetically hold the first and second headgear parts together, a decoupling mechanism comprising a pump associated with the inflatable portion, wherein activation of the pump causes the inflatable portion to inflate, causing the first and/or second part to move away from the other part.

Preferably, the second headgear part has an inflatable portion and activation of the pump causes the inflatable portion to inflate. In one form the parts move away from each other by one or both of the parts moving from a curved configuration to a relatively straight configuration. A substantial portion of each or both of the first and second headgear parts may be inflatable. Preferably the first headgear part and the second headgear part overlap when held together by the magnetic coupling system.

In a further form the respiratory interface or headgear according to any one of the previous aspects comprises a magnet or magnets comprising a segment of solid (non-particulate) magnetic material or a magnet or magnets comprising particulate magnetic material. Preferably the particulate magnetic is material embedded in a part of the respiratory interface or headgear. This may comprise a mask frame and a separate seal module. Preferably the seal module comprises a frame interfacing part formed of a rigid or semi-rigid material and which couples to a mask frame and a seal part formed of a relatively soft material. In one form the interface may comprise an indirect nasal seal or direct nasal seal or an oro-nasal seal. A respiratory interface or headgear having features according to any aspect described herein may comprise any features/integers in combination.

General

Interfaces of the invention may be used in continuous positive airway pressure (CPAP) systems for providing a heated and optionally also humidified air stream to a user (U) through the interface worn by the user, or alternatively in other forms of respiratory systems, such as for example VPAP (Variable Positive Airway Pressure) systems, BiPAP (Bi level Positive Airway Pressure) systems, or in non-invasive ventilation (NIV), or high flow rate (not necessarily also above ambient pressure) therapy, for example, and are described herein generally with reference to CPAP therapy by way of example only. The interfaces may be useful particularly for CPAP therapy at air pressures in the range about 0.5 to about 40 cm $H_2O$. However the interfaces may also be used in in systems or therapy in which the air or other gases are not heated and/or humidified.

In this specification the term "comprising" means "consisting at least in part of". When interpreting a statement in this specification and claims that includes "comprising", features other than that or those prefaced by the term may also be present. Related terms such as "comprise" and "comprises" are to be interpreted similarly.

BRIEF DESCRIPTION OF THE DRAWINGS

Embodiments are described with reference to the accompanying drawings, by way of example and without intending to be limiting, in which:

FIG. 5C is a schematic exploded view of magnet parts of the seal module and mask frame and a gel pad between as will be further described, FIG. 7A is a schematic cross-section view of a seal module and the interfacing part of a mask frame of an interface of another embodiment of the invention, and FIGS. 7B and 7C are schematic views of magnet parts of the seal module and mask frame in correct and incorrect orientations relative to one another respectively, FIG. 12 is a schematic side view of an embodiment of a respiratory interface comprising a nasal seal part and an oral seal part which are detachably magnetically coupled, FIG. 13 is a perspective view form above of an embodiment of an oral insert configured to be retained in a user's mouth when a mask is worn to assist in retaining the mask in position on the face of the user, FIG. 14A is longitudinal cross-section part view of a conduit connected to the end of an elbow of a mask by a magnetic coupling system according to an embodiment, and FIG. 14B is longitudinal cross-section part view similar to FIG. 14A but in which only a part of the conduit is shown in cross-section, FIG. 15 schematically shows an embodiment of headgear for a respiratory interface, comprising headgear parts and a magnetic coupling system arranged to magnetically couple headgear parts to one another, FIGS. 16A and 16B show embodiments of headgear for a respiratory interface comprising a magnetic coupling system to magnetically hold headgear parts together, FIG. 17 shows an embodiment of headgear for a respiratory interface comprising a magnetic coupling system, and a decoupling tool, FIG. 23 is a schematic perspective view of a magnetic coupling feature for a conduit, FIG. 24 is a schematic cross-sectional view of the magnetic coupling feature of FIG. 23, FIG. 25 is a schematic detail cross-sectional view of the magnetic coupling feature of FIG. 23, FIG. 26 is a schematic detailed perspective view of the magnetic coupling feature of FIG. 23, FIG. 27 is a schematic perspective view of headgear in an open configuration, FIG. 28*a* is a schematic cross-section view of the headgear strap taken through plane A-A of FIG. 25 and FIG. 28*b* is a schematic cross-section view of the headgear strap taken through plane B-B of FIG. 27, FIG. 29 is a schematic perspective view of the headgear of FIG. 25 in a wrapped configuration, FIG. 30 schematically shows another embodiment of headgear for a respiratory interface, comprising headgear parts and a magnetic coupling system arranged to magnetically couple headgear parts to one another, FIG. 37 is a schematic cross-sectional view of the seal module and elbow of FIG. 36, FIGS. 38*a* and 38*b* are schematic cross-sectional views of the seal module and elbow of FIG. 36, FIG. 38*a* shows the elbow in a misaligned position and FIG. 38*b* shows the elbow in an aligned position.

DETAILED DESCRIPTION OF SPECIFIC EMBODIMENTS

Figure 1:
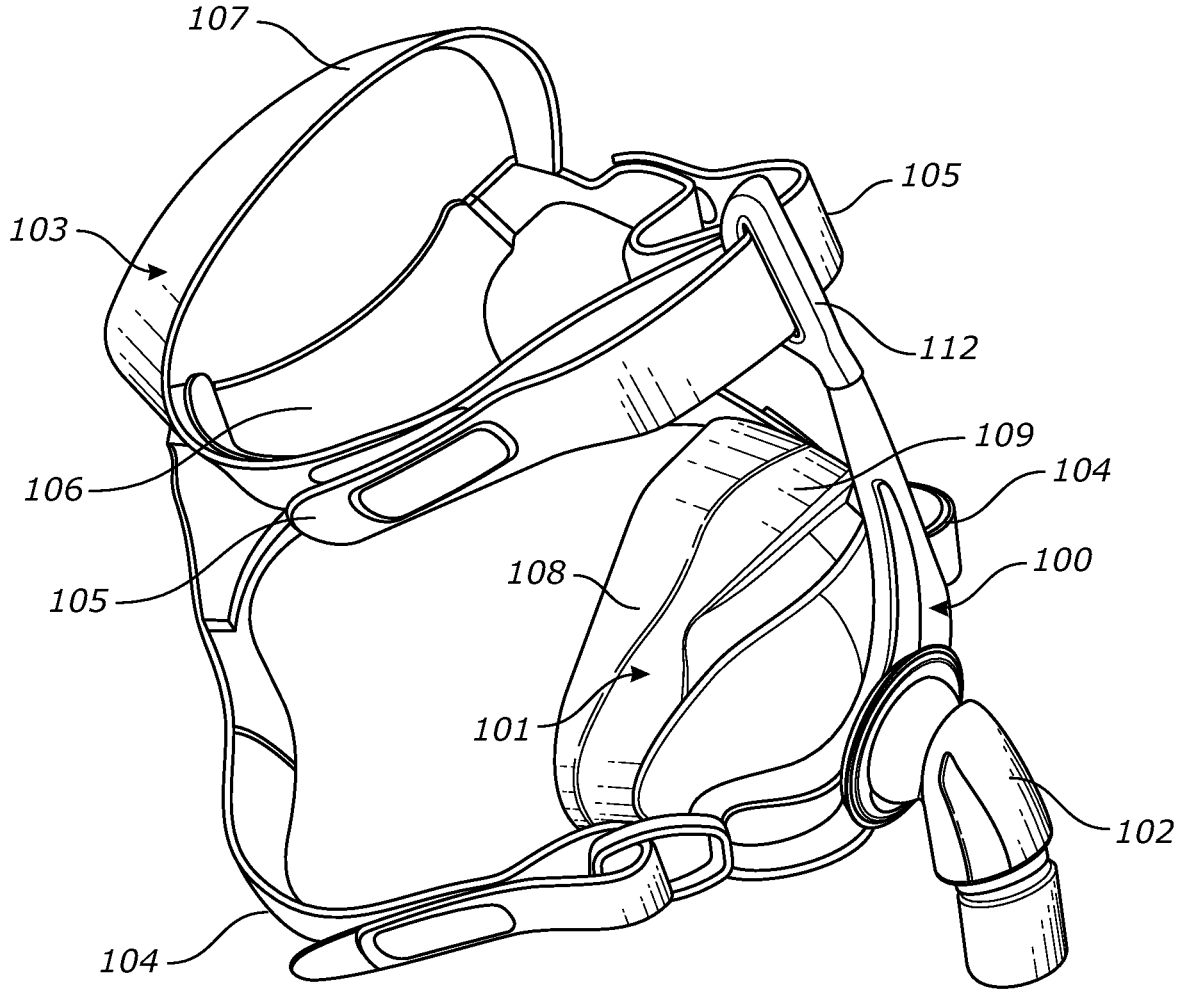
FIG. 1 is a view of an embodiment of a respiratory interface comprising a mask frame and separate seal, and also showing headgear which holds the interface in position on the user's head when worn.
Figure 2:
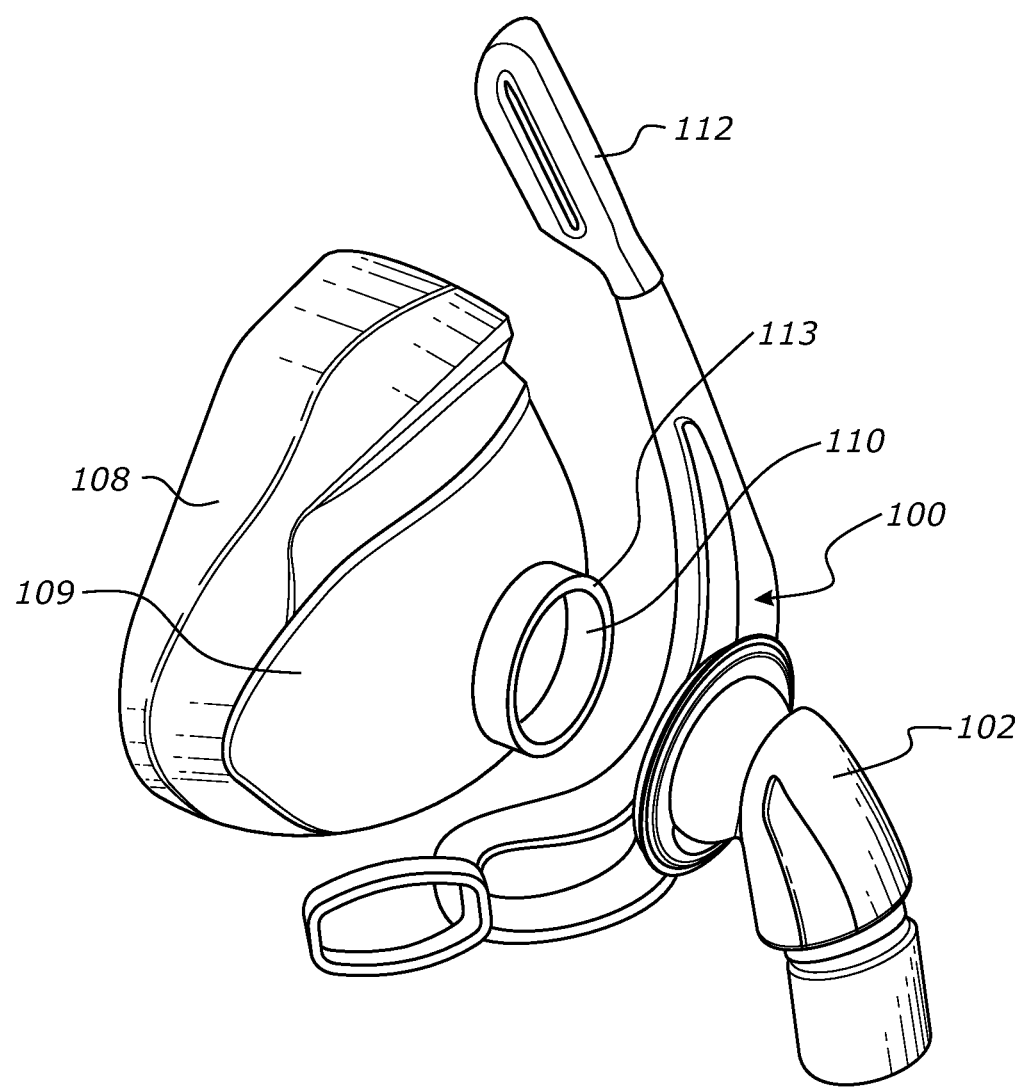
FIG. 2 is a view of the interface of FIG. 1 similar to FIG. 1 (not also showing headgear), showing the mask frame and seal module separated.

Interfaces to which this disclosure relates can be used in the field of respiratory therapy. In some embodiments, the interfaces may have particular utility with forms of positive pressure respiratory therapy. For example, an interface can be used for administering continuous positive airway pressure ("CPAP") treatments, variable positive airway pressure ("VPAP") treatments and/or bi-level positive airway pressure ("BiPAP") treatments. The interface can be compatible with one or more different types of suitable CPAP systems.

Magnetic Coupling of Seal Module and Mask Frame

FIGS. 1 to 4 show a respiratory interface comprising frame 100 and seal module 101. The frame 100 can be rigid, substantially rigid or semi-rigid. For example, the frame can be at least partially made of a metal or rigid plastic, such as acrylic or polycarbonate or high-density polyethylene. The seal module 101 is a separate component from the frame 100 and couples to the user-facing side of the frame to assemble the interface for use, and is detachable from behind the frame for cleaning of the seal module for example. In the embodiment shown in FIGS. 1 and 2 the seal module covers a user's mouth and nose to deliver respiratory gases to the user. Alternatively the seal module may cover the nose only or mouth only, or comprise nasal nozzles or pillows or similar which enter into and seal against or within the nares of the wearer, or cannula which non-sealingly enter the nares. In further embodiments the seal module may cover the mouth and also comprise nozzles or pillows which enter the nares.

In the embodiment shown the interface comprises an elbow 102 by which an air delivery conduit couples to the interface, and in the embodiment shown the elbow couples to the frame 100 via a ball joint but alternatively the elbow may swivel about one axis only, or the air delivery conduit may couple directly to the interface without an elbow. The seal module 101 comprises an aperture into the seal module by which respiratory gases (hereinafter, air) enter the seal module from the elbow or conduit direct.

At least the part of the seal module 101 which contacts the user's face is formed of a soft material, such as a silicone material for example, to comfortably seal against the user's face. All or substantially all of the seal module may be formed from this material, which may be thicker towards and where the seal module interfaces with the frame to provide some structural support to the thinner face contacting part of the seal module, or alternatively as in the embodiment shown a forward part of seal module i.e. a frame interfacing part or shell part 109, may be formed of a rigid material such as acrylic or polycarbonate or high-density polyethylene, or a semi-rigid material (while seal part 108 which contacts the user's face is formed of the softer material). Alternatively again only a smaller part or parts of the seal module which connect the seal module to the frame may be formed of a rigid or semi-rigid material, such as a ring part around the air entry aperture into the seal module for example. Seal part 108 may be overmoulded, welded to shell part 109 or may attach to part 109 by permanent or detachable clipping including snap fitting, for example.

Embodiments of the interface may comprise one or more vent holes for expelling exhaled air. One or more vent holes may be provided in the seal module or elbow 102 for example.

Embodiments of the interface may comprise an anti-asphyxia valve, in an elbow for example or elsewhere on the interface. Headgear generally indicated at 103 holds the interface in position on the user's head when worn. In the embodiment shown the headgear comprises left and right lower straps 104 and left and right upper straps 105, which extend from a rear part 106 of the headgear, along the left and right sides of the user's head below and above the ears to couple to the frame 100 of the interface. The upper straps 105 couple to the top of a forehead support 112 of the frame 100, but in other embodiments may extend downwardly from above the ears, below the eyes, to connect to a frame not having a forehead support. Optionally the headgear may also comprise a top strap such as a crown strap 107 or forehead strap, and/or an occipital loop, and the headgear may be in various other forms. For example headgear may comprise only a rear strap and a crown or forehead strap, and a single strap along either side of the user's head or face to the mask. The rear part 106 of headgear can comprise a generally annular component comprising a back strap, a top strap and a pair of upright straps. The headgear may be formed from parts attached together, using for example ultrasonic welding, or may be a single unitary pieces (not formed from separate attached parts). The length of one or more of the headgear straps may be adjustable. Headgear is commonly formed at least in part from a soft flexible material such as a cloth covered foam material such as BREATHE-O-PRENE® material for example, but may be formed from any other suitable material, such as in whole or part from a semi-rigid plastics material for example which may optionally be covered with a softer material. The headgear may be formed from parts attached together, using for example ultrasonic welding, or may be a single unitary piece (not formed from separate attached parts). The headgear may comprise one or more rounded edges, formed in any suitable manner, for example by applying heat and pressure to edges of the headgear. The headgear assembly can be configured to directly couple to the mask assembly without the use of clips. In some configurations, the pair of upper side straps and the pair of lower side straps can comprise ends with fasteners that loop through headgear attachments on the mask assembly and the fasteners can be configured to couple with complementary fasteners on the sides of the pair of upper side straps and the pair of lower side straps. Further disclosure regarding headgear is at the end of this description.

Figure 3:
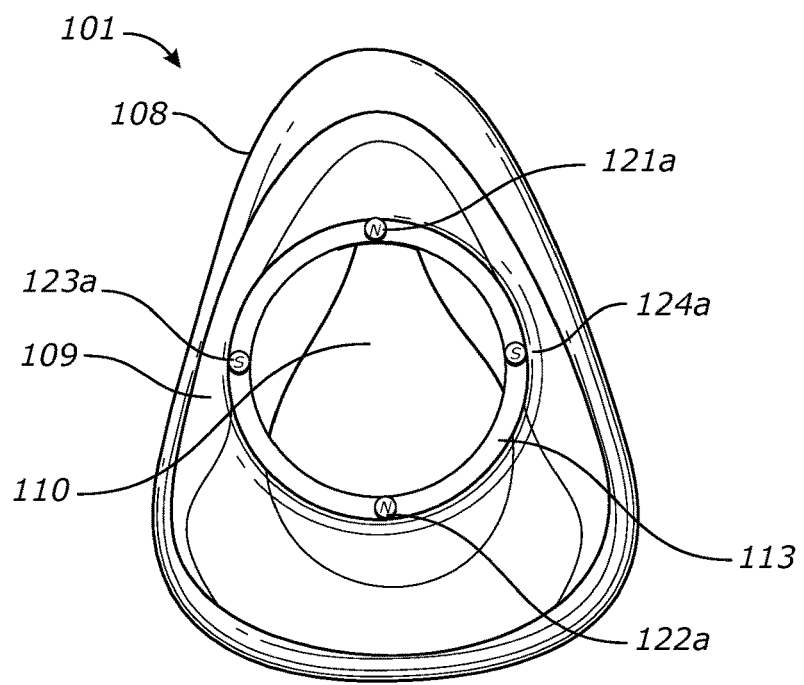
FIG. 3 is a front view of the seal module of the interface of FIG. 1.
Figure 4:
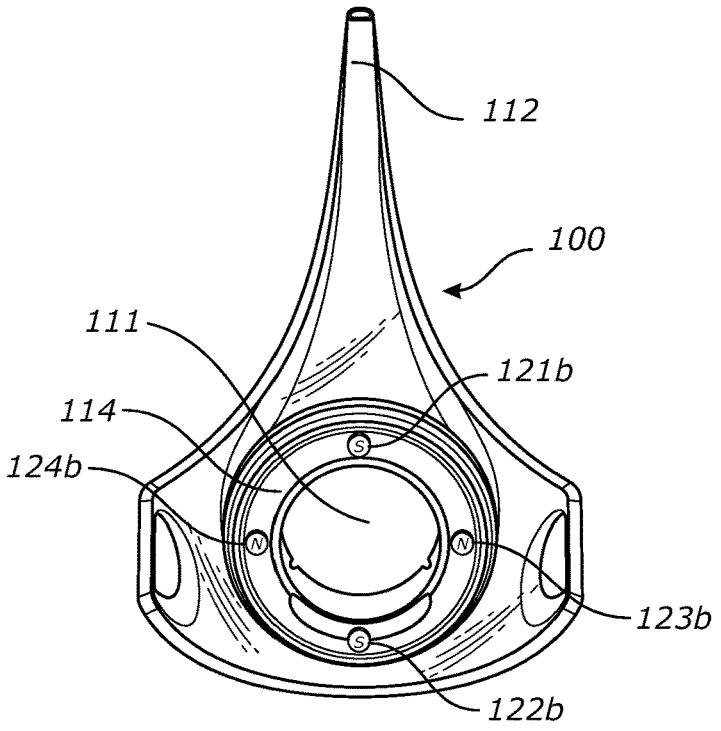
FIG. 4 is a rear view of the mask frame of the interface of FIG. 1, FIGS. 5A and 5B are schematic cross-section views of interfacing parts of a seal module and mask frame of an interface of another embodiment of the invention, separated in FIG. 5A and connected in FIG. 5B.

In the embodiment shown the seal module 101 couples to the mask frame 100 at or around aperture 110 in the front of the seal module through which air enters the seal module in use. When the seal module 101 is correctly fitted to the mask frame 100 seal module aperture 110 aligns with a corresponding aperture 111 through the mask frame from the elbow or conduit, through which air passes to the seal module. In the embodiment shown aperture 111 through the mask frame also defines the socket in the mask frame which receives the ball joint end of elbow 102. A magnetic coupling system couples the seal module 101 and mask frame 100, to hold the seal module on the mask frame. FIG. 3 is a front view of the seal module and FIG. 4 is a rear view of the mask frame i.e. shows the side of the mask frame which interfaces with the seal module. Magnets 121a, 122a, 123a and 124a are associated with rim portion 113 around of aperture 110 through the seal module. For example the magnets may be embedded in this rim portion during plastic moulding of the seal module. Magnets 121b, 122b, 123b and 124b are provided in rim portion 114 around the aperture through the mask frame, and again may for example be embedded in this rim portion 114 during plastic moulding.

The magnets in the seal module and frame are positioned so that when the seal module is positioned against the mask frame in the correct orientation of the seal module and mask frame relative to one another, magnetic attraction will hold the seal module on the mask frame. Thus each pair of magnets 121a-121b, 122a-122b, 123a-123b, and 124a-124b, are provided so that the opposite poles of each pair face one another when the seal module is correctly oriented relative to the mask frame, and then magnetic attraction holds the seal module and mask frame together. It is preferred to provide magnets in both the seal module and mask frame, but alternatively magnets may be provided in the seal module only and a ferrous component or components provided in the mask frame (about aperture 111), or vice versa, or some magnets may be provided in each of the seal module and mask frame and also ferrous components at other locations in each of the mask frame and seal module. At least one magnet or ferrous component is provided in the seal module and at least one ferrous component or magnet in the mask frame, or at least one magnet in each of the seal module and mask frame. In the embodiment shown four magnets are provided in each of the seal module and mask frame, approximately equidistantly spaced about the apertures 110 and 111 as described.

In at least some embodiments at least two magnets are provided in the seal module 101 and at least two matching magnets in the mask frame 100, and the two magnets in the seal module have opposite poles facing the mask frame and the same for the two magnets in the mask frame facing the seal module. For example in the embodiment shown in FIGS. 3 and 4, magnets 121a and 122a in the seal module 101 have north poles facing the mask frame, and magnets 123a and 124a have south poles facing the mask frame. Magnets 121b and 122b in the mask frame 100 have south poles facing the seal module and magnets 123b and 124b in the mask frame have north poles facing the seal module. Thus in the correct orientation of the seal module and mask frame relative to one another all magnets attract, to hold the seal module on the mask frame, but if the seal module is offered to the mask frame in at least one or more incorrect orientations, the magnets repel. The magnets may be arranged so that a seal module will couple to the mask frame only in one (correct) orientation of the seal module relative to the mask frame. Such an orientation may be achieved by an asymmetrical arrangement of magnets upon the seal module, coupling to an identical asymmetrical arrangement of opposite pole magnets upon the mask frame.

Figure 6:
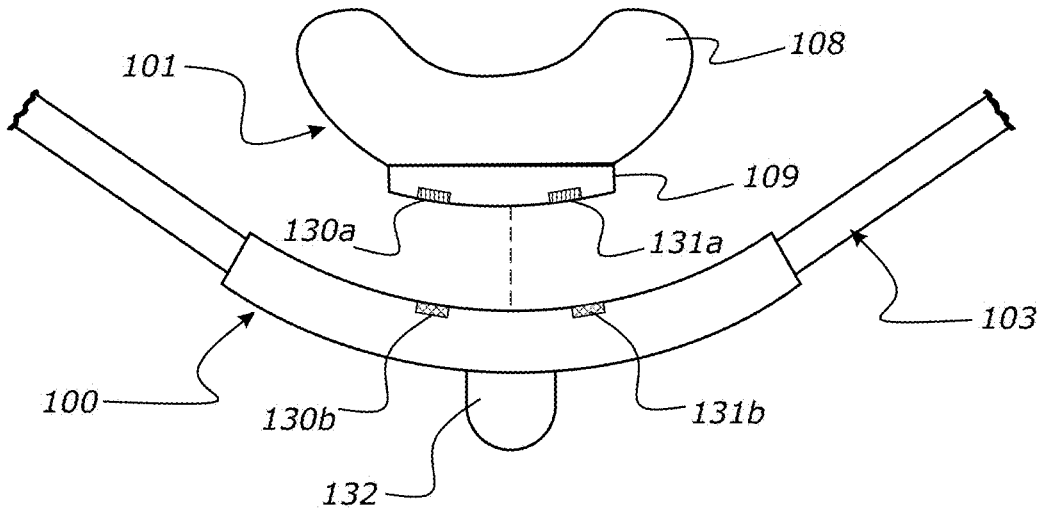
FIG. 6 is a schematic cross-section view of a seal module and the interfacing part of a mask frame of an interface of another embodiment of the invention.

FIG. 6 shows another embodiment of an interface, in which magnet 130a on a right hand side (as the interface is worn) of seal module 101 has its north pole facing mask frame 100 and magnet 131a on a left side of the seal module has its south pole facing the mask frame. Magnet 130b on right side of the mask frame 100 has its south pole facing the seal module 101 and magnet 131b on left side of the mask frame has its north pole facing the seal module 101. Two such magnets are provided in each of the seal module 101 and mask frame 102. The seal module 101 will only magnetically couple to the mask frame 100 when the seal module is offered to the mask frame 100 in the correct orientation, such that magnet 130a is opposite magnet 130b and magnet 131a opposite magnet 131b. In other orientations of the seal module relative to the mask frame, either the magnets will not align so that there will be no magnetic attraction of the seal module to the mask frame, or in a reversed (upside down) orientation of the seal module, magnets 131a and 130a in the seal module will face magnets 130b and 131b in the mask frame and the magnets will magnetically repel, so that the seal module and mask frame cannot be coupled together, making it apparent to the user that the orientation of the seal module relative to the mask frame is incorrect. Unless otherwise indicated in this and later figures similar reference numerals as in FIGS. 1 to 4 indicate similar components.

FIG. 7A is a schematic view of a seal module 101 which comprises nozzles 101a and interfacing part of a mask frame 100 of an interface of another embodiment of the invention, such as a frame rim 114, and FIGS. 7B and 7C are schematic views of magnet parts of the seal module and mask frame in correct and incorrect orientations relative to one another respectively. Three magnets 141a, 142a and 143a are provided in the seal module 101, and three magnets 141b, 142b and 143b in opposite locations in the mask frame. Magnets 141a and 142a in the seal module have similar poles facing the mask frame e.g. north poles. Magnet 143a in the seal module has an opposite pole facing the mask frame (opposite to magnets 141a and 142a) e.g. south pole. Similarly in the mask frame magnets 141b and 142b have similar poles facing the seal module e.g. south poles, and magnet 143b has an opposite pole facing the seal module e.g. north pole. Thus the seal module and mask frame will attract only in one (correct) orientation of the seal module relative to the mask frame, as illustrated by FIGS. 7B—correct orientation, and 7C—incorrect orientation.

Interfaces of the invention may rely solely on magnetic coupling of the seal module to the mask frame in use of the interface. Alternatively a magnetic coupling system may supplement, and be provided in addition, to mechanical coupling between the seal module and the mask frame, such as a friction fit, snap fit, or other interference fit, of formations on the seal module and mask frame to one another, either around the airway path through the mask frame into the seal module, or at other locations on the seal module and mask frame.

In some embodiments the interface may rely predominantly on mechanical coupling to hold the seal module on the mask frame, and a magnetic coupling system as described may be provided primarily to indicate correct and incorrect alignment of the seal module and mask frame when the user brings them together, so that coupling can only occur when the seal module and mask frame are offered to one another in correct alignment.

Figure 9A:
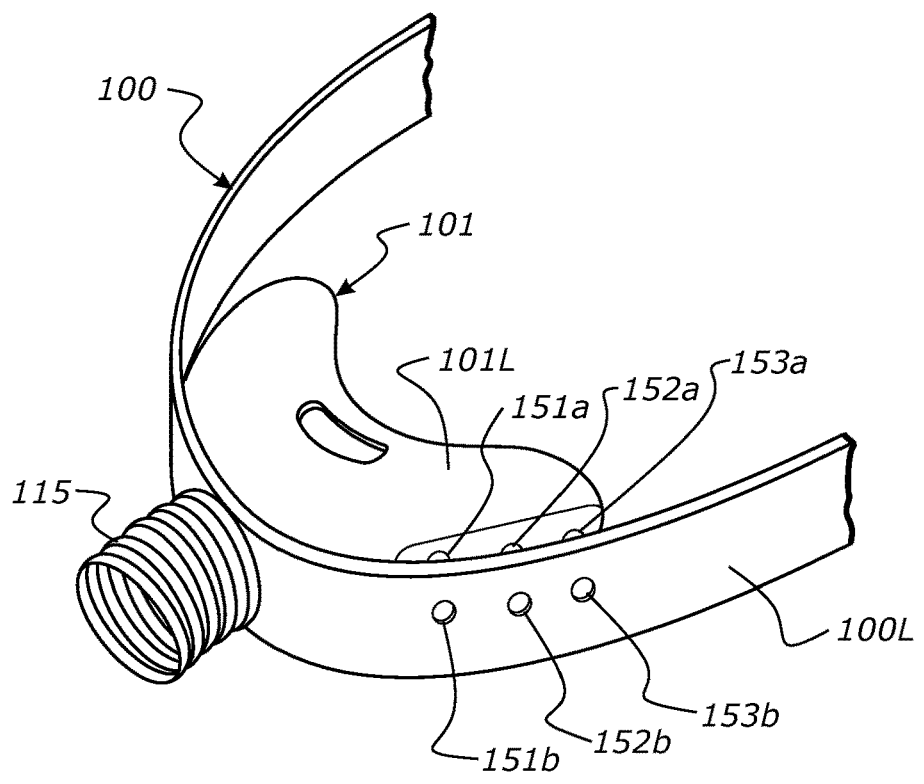
Figure 9B:
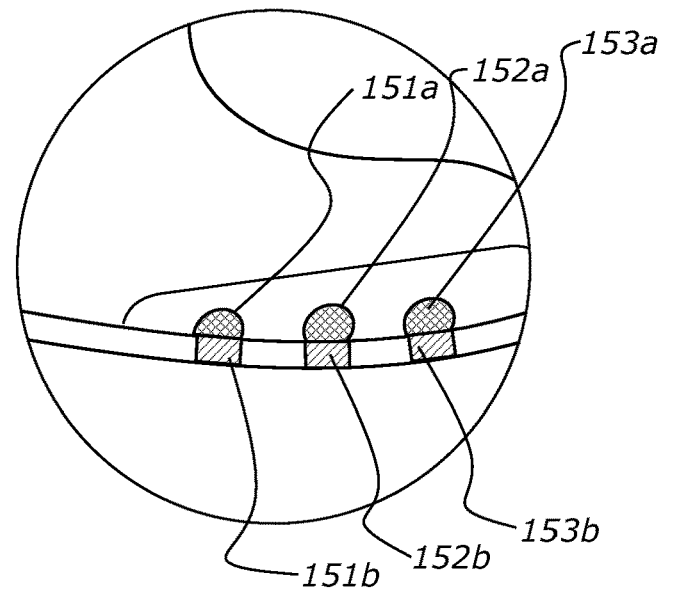
Figure 10:
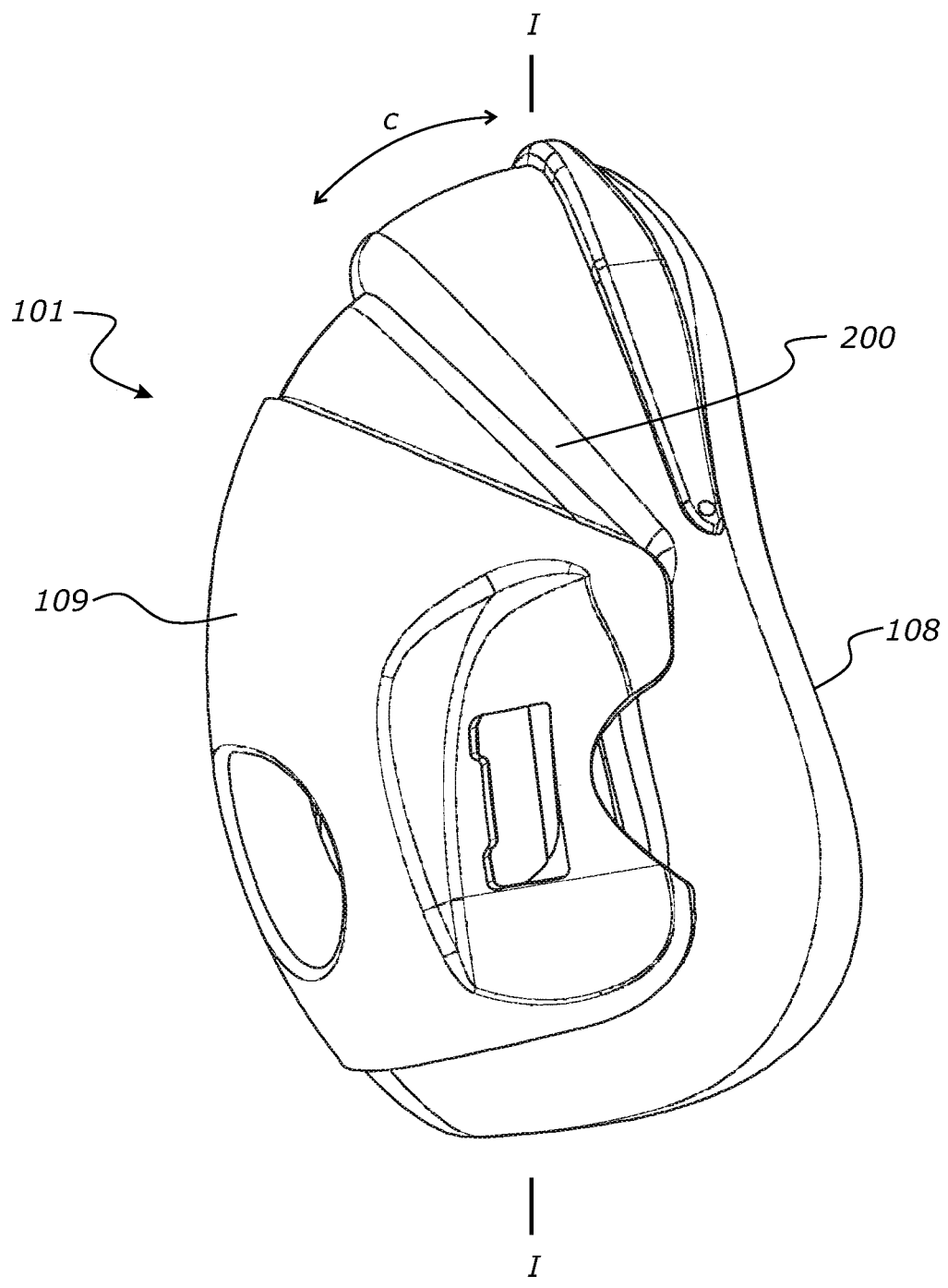
FIG. 10 is a side view of a seal module of a further embodiment of the invention.

FIGS. 9A and 9B are schematic views of an embodiment of a respiratory interface in which magnets associated with the seal module and mask frame are provided not directly around the airway path, but at left and right sides of the seal module and mask frame. In this embodiment one or more magnets, such as magnets 151a, 152a, and 153a, are provided on the left side 101L of the seal module, which couple to one or more magnets (or ferrous parts), such as and magnets 151b, 152b and 153b, on the side of a left part 100L of the frame of the mask. Similar magnets are provided on the right side of the seal and corresponding right side of the frame (not shown). The magnets attract when the seal module and mask frame are correctly aligned relative to one another. Around the airway path connection i.e. the connection of an air entry aperture centrally positioned into the seal module 101, to an aperture through mask frame 100 from the conduit 115, formations may be provided for a mechanical connection between the seal module and mask frame, to hold or assist in holding the seal module to the mask frame, or alternatively coupling of the seal module to the mask frame may rely primarily on the magnetic coupling system and simply a gas seal may be provided between the seal module air gases entry aperture and the mask frame to prevent air leakage. In the embodiment shown the seal is an under-nose indirect seal but may be any other seal type as previously described.

Figure 8A:
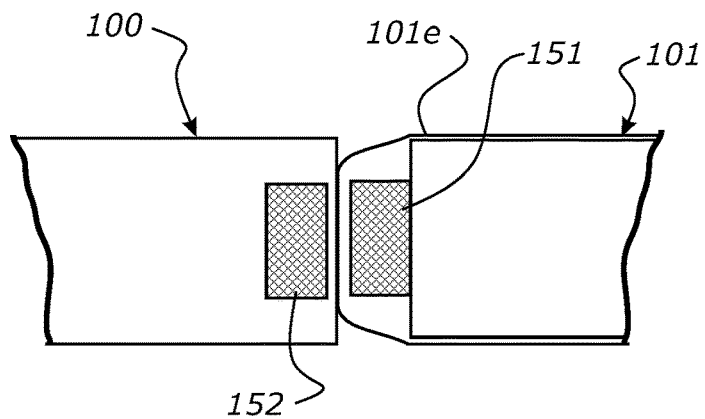
FIGS. 8A, 8B, and 8C are schematic cross-section views of interfacing parts of a seal module and mask frame of an interface of a further embodiment of the invention, connected in FIG. 8A, near connected in FIG. 8B, and apart in FIG. 8C, FIGS. 9A and 9B are schematic views of an embodiment of a respiratory interface of the invention in which magnets associated with the seal module and mask frame are provided at left and right sides of the seal module and mask frame.
Figure 8B:
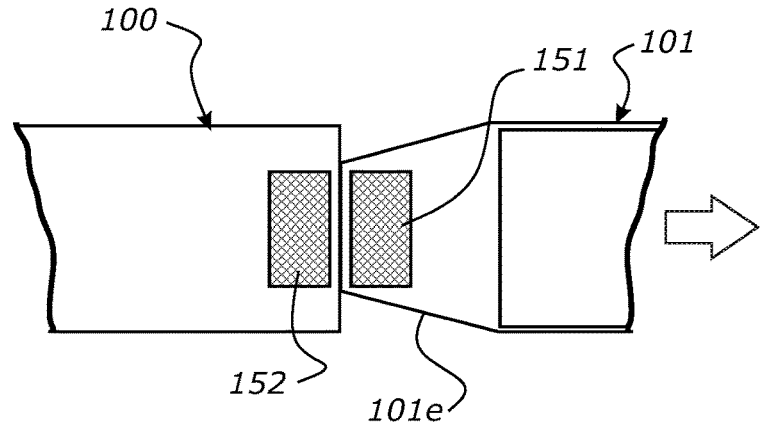
Figure 8C:
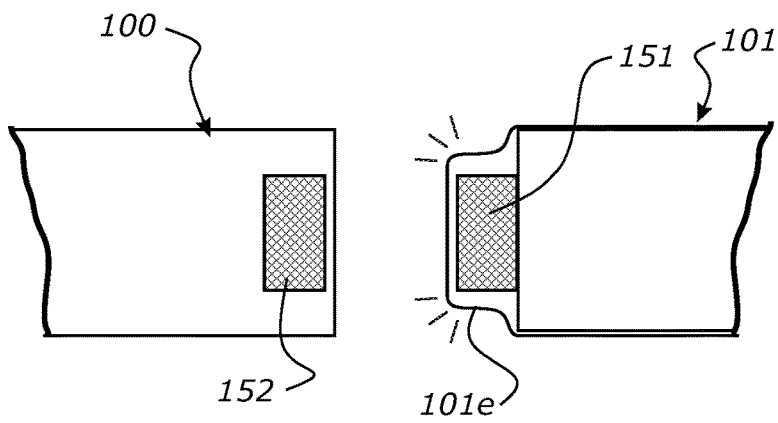

FIGS. 8A, 8B, and 8C are schematic cross-section views of interfacing parts of a seal module and mask frame of an interface of a further embodiment of the invention. The objective of this embodiment is to produce an audible sound (e.g. 'click') on attachment and detachment of the seal module to/from one another. The interfacing parts of the seal module and mask frame are shown connected in FIG. 8A, near connected in FIG. 8B, and apart in FIG. 8C. In this embodiment magnet or magnets 151 associated with the seal module 101 for example about the periphery of an air entry aperture into the seal module, are mounted to the seal module such that they can move relative to the balance of the seal module, in the direction of the arrow in FIG. 8B between the magnet position shown in FIGS. 8A and 8C, and the magnet position shown in FIG. 8B. For example the magnet(s) 151 may be embedded in a part 101e of the seal module designed to contact the mask frame 100, which part of the seal module is formed of a stretchable material. For example the seal module may be moulded from a soft synthetic elastic material; the magnets are embedded in the soft material; and the soft material around the magnets is elastically stretchable so that the magnets can move relative to the balance of the seal module. Alternatively the magnets may be captured on for example a rim of the seal module by an elastically stretchable fabric cover.

FIG. 8A shows the seal module 101 connected or coupled to the mask frame. FIG. 8C shows the seal module and mask frame separated. The normal position of the seal magnet(s) is as shown in FIG. 8B. When the seal module is offered to the mask frame, as the seal module approaches the position shown in FIG. 8C relative to the mask frame, and continues to approach the mask frame, magnetic attraction will pull the magnet(s) of the seal module towards the magnet(s) 152 of the mask frame, stretching the magnet(s) 151 of the seal module away from the balance of the seal module as shown in FIG. 8B, until they contact the mask frame (then pulling the seal module fully towards the mask frame to the fully coupled position shown in FIG. 8A). As the seal module is brought towards the frame, at a break point at which the magnetic attraction of the seal and frame magnets to one another exceeds the elastic retractive force of the elastic part or stretchable fabric cover 101e of the seal module, the seal magnet(s) 151 will snap from the position of FIG. 8C to that of FIG. 8B and the impact of the seal module magnet(s) against the frame or frame magnets may produce an audible click. Similarly when the seal module is pulled from the mask frame i.e. the seal module is moved from the position shown in FIG. 8B to that shown in FIG. 8C, the magnet(s) 151 of the seal module will come away from the mask frame and snap back into position as shown in FIG. 8C which may again producing an audible click. Alternatively the magnet (s) (or ferrous part(s)) on the frame may be elastically movably mounted, or the magnets on both the seal module and frame. It may be advantageous that the magnet(s) movement as described produces an audible sound on coupling and uncoupling as an indicator to the user but in other embodiments the same structures as described may be employed but designed to couple and uncouple silently.

FIGS. 5A and 5B are schematic cross-section views of interfacing parts of a seal module and mask frame of an interface of another embodiment, separated in FIG. 5A and connected in FIG. 5B, and FIG. 5C is a schematic exploded view of magnet parts of the seal module and mask frame and a gel pad between as will be further described. This embodiment is similar to others previously described in which magnets or magnets and one or more ferrous components are provided on a seal module 101 and mask frame 100 about the airway path through the interface. In this embodiment a ring 160 of a compressible material is provided on the seal module 101 forward of the magnet(s) 161 about the seal module gases entry aperture 110 as shown. The compressible ring 160 may for example comprise a ring of captured gel i.e. gel captured in an annular membrane, or a compressible synthetic material or rubber ring for example. FIG. 5A shows the seal module 101 and mask frame 100 separated and FIG. 5B shows the seal module and mask frame coupled. When the seal module and mask frame are coupled the compressible ring 160 is between the magnet(s) 161 and 162 on the seal module and the mask frame, and may be compressed slightly. This may assist in ensuring an airtight seal between the seal module and mask frame for example.

In the embodiment shown a single magnet is provided on each of the seal module and mask frame, each in the form of a ring magnet as shown in FIG. 5C. Alternatively the magnets 161 and 162 on one or both of the seal module and mask frame may comprise two or more curved segments which collectively define a ring around the airway path through each of the seal module and mask frame, or alternatively again the magnets may be multiple smaller individual magnets as shown for other embodiments.

In each case and in any embodiment of the invention, a magnet or magnets may comprise a segment of solid (non-particulate) magnet material, or alternatively a particulate magnetic material i.e. particles of a magnetic material embedded by plastic moulding for example, for example in the seal module or mask frame. Particulate material may form a ring magnet as in FIG. 5 or multiple individual magnets as in other embodiments.

FIGS. 39-41 and FIGS. 42A-42C show a further embodiment of seal module to mask frame magnetic coupling that allows a method of replacing or switching seal modules without removal of headgear from a user.

Figures 39, 40, 41:
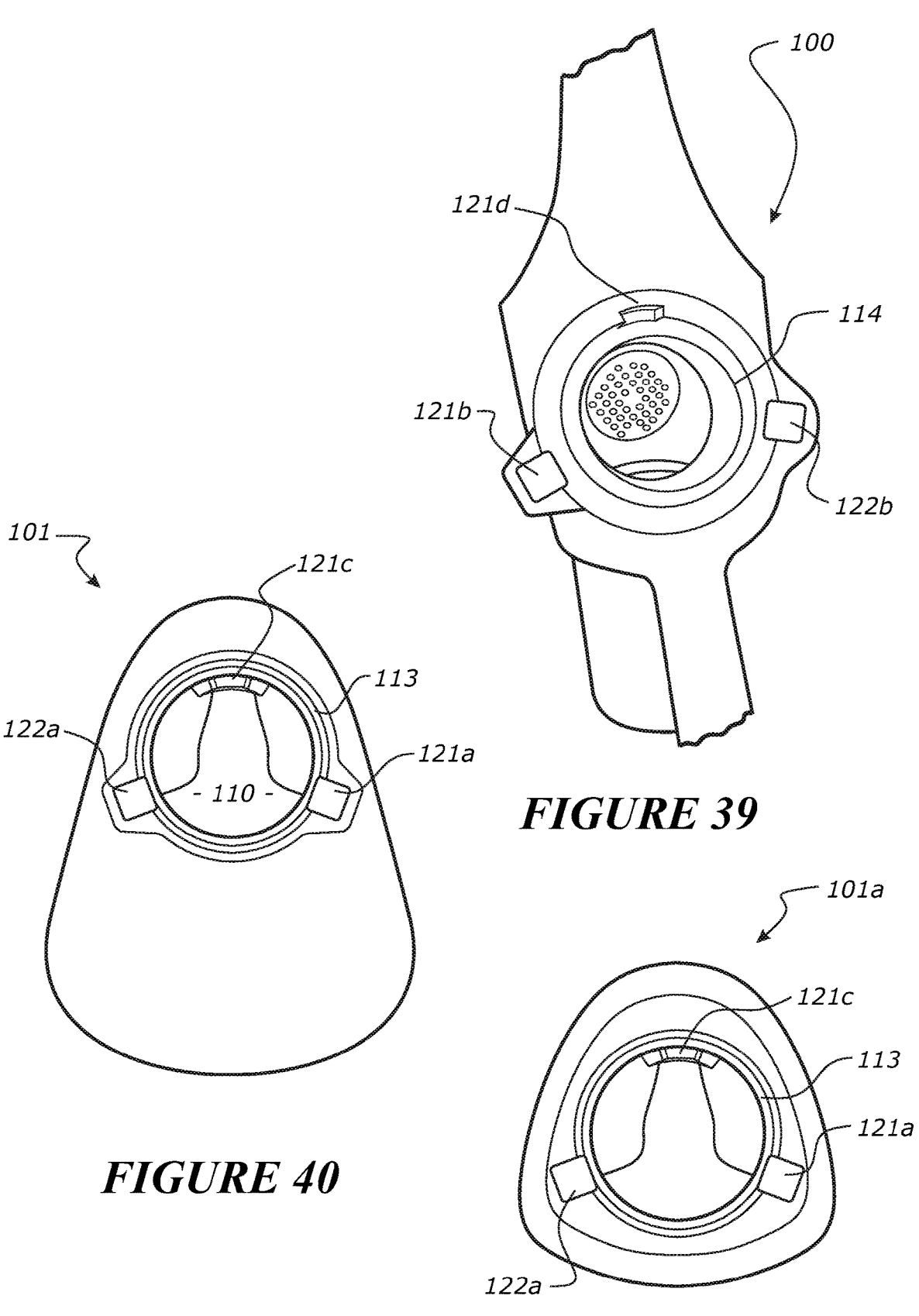
FIG. 39 shows a rear view of a mask frame according to another embodiment.
FIG. 40 shows a first seal module for use with the mask frame of FIG. 40.
FIG. 41 shows a second seal module for use with the mask frame of FIG. 39, FIGS. 42A to C show a sequence of interchanging first and second seal modules with a mask frame according to FIG. 39 and seal modules according to FIGS. 40 and 41.

FIG. 39 is a rear view of a mask frame 100 i.e. shows the side of the mask frame which interfaces with the seal module, comparable to FIG. 4; meanwhile FIG. 40 is a front view of a seal module 101 for covering the nose and mouth of a user, comparable to FIG. 3. Magnets 121a and 122a are set into recesses on the seal module 101. The magnets 121a and 122a are located on opposite sides of an aperture 110 through the seal module 101. Surfaces of the magnets are flush with an outer surface of the seal module. This outer surface is a surface of radial flanges associated with a rim portion 113 of the seal module around the aperture 110. In the illustrated form magnets 121a and 122a are arranged opposite each other at a lower portion of the rim portion 113. The positions of the magnets 121a and 122a may be described as being at approximately four and eight o'clock positions respectively. The seal module also comprises a locator 121c in an upper portion. The locator is in an uppermost position upon the seal module 101. The position of the locator 121c may be described as being at approximately a 12 o'clock position. The magnets 121a and 122a are equidistantly spaced from the locator 121c.

Corresponding magnets 121b and 122b are likewise set into recesses in the mask frame 100. The magnets are located on opposite sides of an aperture through the mask frame. The magnets 121b and 122b on the mask frame are located so that they will be opposed to and engaged with respective magnets 121a and 122b on the seal module 101 when the seal module is joined to the mask frame. Surfaces of the magnets are flush with an inner surface of the mask frame. This inner surface is a surface of radial flanges associated with a rim portion 114 of the mask frame around the aperture. In the illustrated form magnets 121b and 122b are arranged opposite each other at a lower portion of the rim portion 114. The positions of the magnets 121b and 122b may be described as being at approximately four and eight o'clock positions respectively. The mask frame also comprises a locator 121d in an upper portion. The locator is in an uppermost position upon the mask frame. The position of the locator 121d may be described as being at approximately a 12 o'clock position. The magnets 121b and 122b are equidistantly spaced from the locator 121d.

Although the illustrated embodiment shows the seal module and mask frame having two magnets and a single locator, it is to be appreciated that in other embodiments, the seal module and mask frame could each have 3, 4, 5, 6, 7, 8 or more magnets and/or 2, 3, 4, 5, 6, 7, 8 or more locators.

Locating features 121c and 121d may have any suitable mating profiles that enable the locating features to inter-engage with each other. The profiles for the locating features may be shaped with keys that limit fitment between the locating features to particular orientations. The locator 121c on the seal module is a projection (male part) that projects forwardly of the seal module. The locator 121d on the mask frame is a recess (female part) that extends into the mask frame. The recess locator 121d is configured to receive the projection locator 121c. It is to be appreciated that in other embodiments, the locator on the seal module may be a recess and the locator on the mask frame may be a projection. The locator projection 121c has a wedge shape. That is, the locator projection 121c tapers as it extends away from the seal module. Such a wedge shape enables guidance of the locator projection into the locator recess and subsequent engagement of the magnets even when the seal module and mask frame are not perfectly aligned.

When the seal module is coupled to the mask frame, the receipt of the projection locator 121c in the recess locator 121d provides resistance to rotation of the seal module relative to the mask frame about the seal module aperture. However, the inter-engagement of the locators provides no limitation to linear movement of the seal module away from the mask frame. The engagement of the respective magnets 121a,b and 122a,b on the seal module and the mask frame, provides resistance to the linear movement of the seal module away from the mask frame but is weak at resisting rotation of the seal module relative to the mask frame about the seal module aperture. Accordingly, the locators and magnets provide a combination of mechanical and magnetic engagements to hold the seal module to the mask frame. The locators and magnets provide threshold resistance to disen-gagement of the seal module from the mask frame under rotation or linear forces. The threshold rotation force in a direction about the seal module aperture to cause disengage-ment is higher than the threshold linear force.

FIG. 41 shows a nasal seal module 101a that otherwise has the same configuration of magnets 121a, 122a and locating feature 121c about a rim portion 113 as the full nose/mouth seal module 101 of FIG. 40. In this way it is compatible to be coupled with the rear of the same mask frame 100 shown in FIG. 39.

Figures 42A, 42B, 42C:
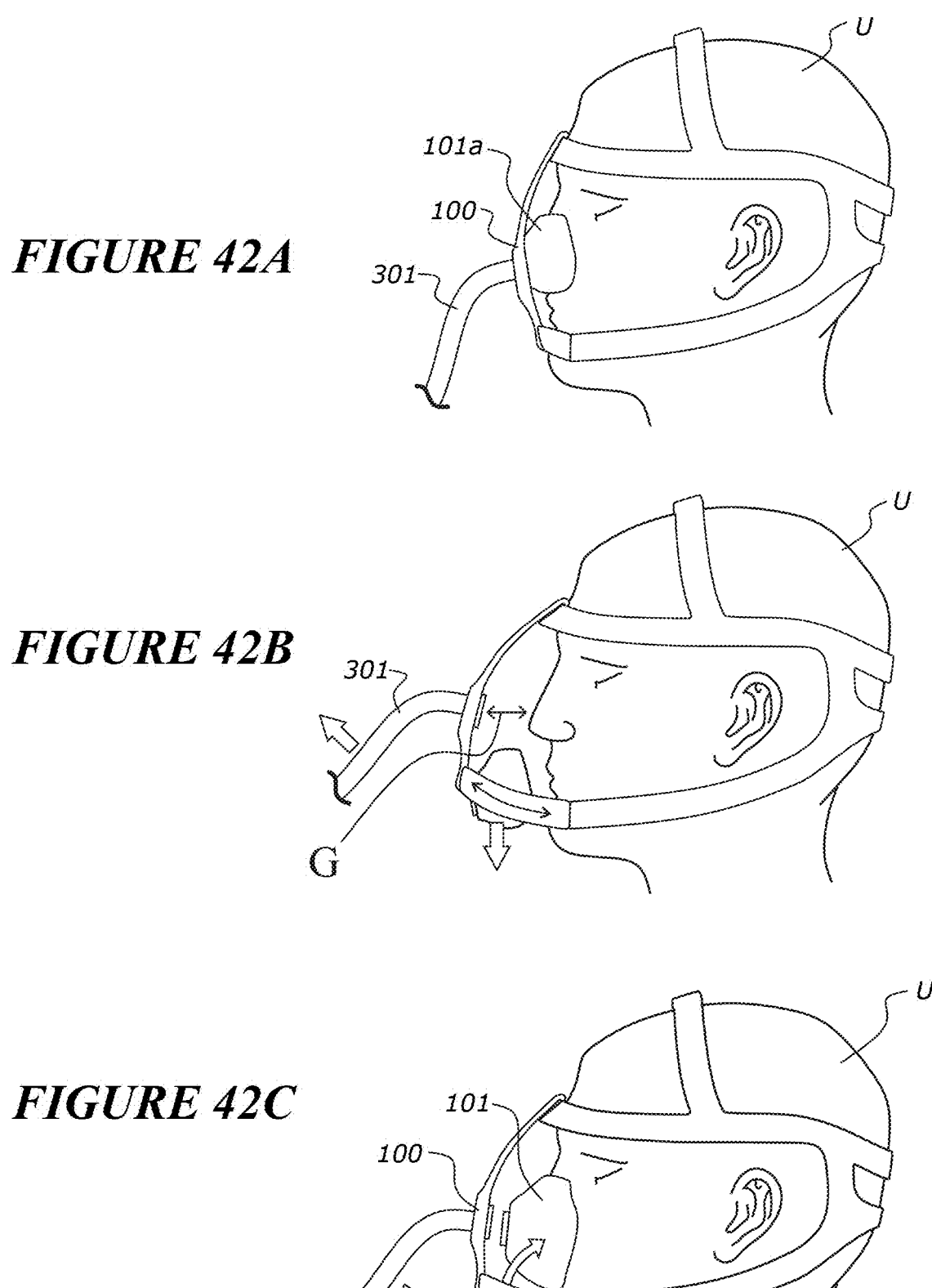

FIGS. 42A-C illustrate a method that can be implemented using the mask frame 100 and seal module components 101 and 101a and, particularly, a method of swapping seal module components without removal of the headgear.

A user U is shown in FIG. 42A wearing headgear and a nasal seal module 101a in place upon mask frame 100. Headgear can be exemplified according to principles dis-closed in the Applicant's PCT Publication No. WO2014/175752, the entire contents of which are incorporated herein by reference. e.g. paragraphs [0145]-[0149], [0159]-[0163], wherein with respect to patient interfaces that seal on the face of the user, the interface (e.g., mask) in cooperation with the user's face creates a sealed chamber. Pressurized breathing gases are delivered to the sealed chamber, which generates a force tending to move the mask away from the user's face. This force is generally equal to the (projected) seal area multiplied by the positive pressure and is often referred to as the "blow-off force. A function of the headgear is to restrain the mask in response to the blow-off force to keep the mask in equilibrium sealed against the face of the user. The blow-off force stresses the headgear in an attempt to elongate it, which places the headgear under tension.

In addition, the headgear applies a force to the user's head over an area with which the headgear is in contact. The force applied to the contact area can be referred to as the "skin pressure" of the headgear. As the air pressure within the chamber defined by the seal or the combination of the seal and the frame increases, the force applied by the headgear attempts to restrain the interface assembly from lifting from the face. As such, the force applied by the headgear generally will increase to oppose the increasing force resulting from the increasing pressure within the mask. The blow-off forces will vary for different types and sizes of interfaces at any given pressure. Nevertheless, at lower pressures, or no pressure in the case of cannulas, less force is required to oppose the blow-off forces.

Accordingly, headgear assemblies preferably can be designed to achieve a "balanced fit." In some configurations, the headgear assemblies generally comprise a stretch component (also referred to as elastic), a non-stretch component (also referred to as inelastic or non-elastic), a mechanism that restricts extension of the headgear, and a coupling that can join the headgear assembly to the mounting points, for example but without limitation. In at least some configurations, the balanced fit can be achieved by creating a sub-stantially non-stretch path to resolve the stresses in the headgear when in use or in response to normal operational forces (e.g., blow-off and/or hose pulls forces, plus a reserve, if desirable). At higher forces than seen in use, the headgear can exhibit stretch-like behaviour for donning. In some configurations, the headgear assembly may not include a stretch component. For example, the headgear could be manually extended and retracted.

The stretch components, when present, can have any suitable configuration. The stretch components can be any component that has a tensile modulus of less than about 30 MPa. The tensile modulus is the mathematical description of the tendency to be deformed elastically (i.e., non-perma-nently) along an axis when forces are applied along that axis; tensile modulus is the ratio of stress to corresponding strain when a material behaves elastically. In some configurations, the stretch component can be a coated, spun yarn material and the stretch component can include materials such as, but not limited to, rubber and spandex or elastane (e.g., LYCRA). In some configurations, the stretch component can be a strap or a combination of straps. In some configurations, the stretch component can be formed of a stretchable or elastic material. In some configurations, the stretch compo-nent enables the headgear to be expanded or lengthened and the stretch component also provides a retraction force that serves to contract or shorten the headgear. The contraction, or shortening, can occur as a result of the elastic properties of the stretch component. The contraction, or shortening, allows the headgear to more closely match the user's head circumference (plus the size of the mask). Generally, the headgear length is defined by a relaxed length and the headgear seeks to return to that length and it is this returning toward the relaxed length after elongation that is meant by contraction unless otherwise apparent.

The non-stretch components can serve as a stretch limiter. The non-stretch components can have any suitable configu-ration. In some configurations, the non-stretch components have a higher modulus of elasticity compared to the stretch components. The stretch components can be any component that has a tensile modulus of more than about 30 MPa. In some configurations, the non-stretch components restrict elongation of the headgear due to forces that are lower than a specified yield force. In some configurations, the yield point of the non-stretch material is higher than any antici-pated loading to be applied to the headgear. In some con-figurations, the non-stretch components resist elongation of the headgear once the headgear has been fitted to the head. In some configurations, the non-stretch components resist elongation of the headgear once the headgear has been fitted to the head and the CPAP pressure has been applied to the mask. Thus, in some configurations, the non-stretch com-ponents (in some cases, in combination with the mecha-nisms discussed below) can thwart or resist elongation of the stretch components at least when CPAP pressure is applied. In the case of a cannula, the non-stretch components can resist the movement of the cannula under the influence of external forces, such as hose pull.

The mechanism can be any suitable mechanism that can limit expansion or elongation of the headgear when a force lower than a specified yield force is applied to the headgear. In some configurations, the mechanism operates without an effort by the user (e.g., the mechanism is automatic). That is, in at least some configurations, the mechanism can auto-matically move or switch to a mode in which extension or expansion is limited below the specified yield force. How-ever, effort may be required for the user to don the mask, such as effort above the yield force to extend the headgear. In some configurations, the mechanism can apply a motion resistance force that can limit the extension or expansion of the headgear when a force lower than the specified yield force is applied to the headgear. In some such configura-tions, the motion resistance force can be a friction force. The specified yield force, that is, the force at which the headgear mechanism's motion resistance forces are overcome and elongation of the headgear becomes possible, may be deter-mined by (1) the maximum blow-off force that is possible for the specific mask in use when a range of about 4-20 cm H2O pressure is anticipated and (2) a reserve to allow for any pulling of the CPAP hose and differences in user fit preferences. The reserve, generally defined as the difference between the lengthening or extension force and the maxi-mum balanced fit force, can provide a buffer above the balance fit force, in which additional forces can be applied to the headgear without substantial elongation of the head-gear occurring. The reserve force component can compen-sate for any additional force, such as hose pull, that may act to pull the headgear from the user's head. In some configu-rations, the motion resistance force can be applied to restrict extension of the headgear while releasing to allow retraction or contraction of the headgear. In some configurations, the mechanism can use one-way friction to lock or otherwise secure the headgear length. For example, the length can be secured using a factional force that can only be overcome by a force that exceeds the blow-off force with minimal exten-sion. Such mechanisms can be referred to herein as a directional locking arrangement or directional lock. The term "lock" as used herein is intended to cover mechanisms that secure the headgear length in response to certain forces, such as blow-off forces and/or hose pull forces. A "lock" does not necessarily secure the headgear length in response to all forces. Preferably, in some configurations, the reten-tion force of the lock ("lock force") can be overcome, such as by manually-applied forces during the application portion of the fitment process.

To remove the interface while wearing the headgear described below, the seal can be pulled forward with a force greater than the mechanism's maximum holding force. This causes the headgear to lengthen and which enables the seal to be pulled away from the face and over the user's head. Once removed, the lack of forces on the headgear will cause the headgear to automatically retract to its relaxed size.

In some configurations, the headgear applies a three phase force extension fit profile. In the application phase, the headgear is stretched to go over the head of a user. A load curve features a steep rise in load for the initial extension of the headgear that then transitions to a generally constant, flat extension curve as the headgear is further stretched to accommodate larger head circumferences. In the adjustment phase, the headgear retracts and returns from a stretched condition until a desired fit is achieved. The load curve shows an initial decrease in load as the headgear retracts to fit onto the user's head and also illustrates a low load force as the headgear further retracts to fit the user's head circumference. In the third phase, the balanced fit phase, the headgear adjusts to hold its position on the user's head as CPAP pressure is applied. The load curve illustrates that a rise in load force of the headgear balances with the blow-off force due to the CPAP pressure and also resists additional forces, such as hose pull. In the case of a cannula embodiment, a balanced fit can be achieved at the end of phase two, and phase three typically will only be initiated if and when an external force, such as hose pull, is experienced.

As discussed above, the load curve will have a steep rise because the headgear has initial resistance to stretch as it is stretched to accommodate the user's head. The initial resistance can relate to overcoming the resistance that will resist elongation. Once the load has reached a yield force of the mechanism of the headgear, the load curve transitions to a substantially flat, generally constant extension curve as the headgear stretches further with little increase in load force for greater amounts of headgear extension.

In the second phase, the headgear has been sufficiently stretched or elongated to fit over the user's head and the headgear has been released into position. Once a desired positioning has been achieved, the headgear returns from the stretched condition (e.g., over-elongated position) and the load force sharply declines. After this reduction in force due to retraction of the headgear to fit the user's head, the load curve remains low 226 as the headgear remains fitted to the user's head. The headgear that typifies many features, aspects and advantages of the present invention features a first high load required to cause elongation and a second lower load at which the headgear contracts. In other words, the headgear contracts at a lower load than required to cause elongation and a hysteresis is the provided effect. In some configurations, the headgear has a delay in length change while the force changes dramatically when changing from an elongation mode to a contraction mode. In some configurations, the change in length of the interface circumference (including the headgear assembly) lags behind changes in load (i.e., force) when the interface length changes from elongation to contraction. Moreover, in some configurations, during elongation, as the force increases, the length increases more than the decrease in length during the decrease in force.

A balanced fit is achieved in the balanced fit phase, in which the force of the headgear balances the blow-off force of the CPAP pressure. As mentioned above, the headgear adjusts to hold its length as CPAP pressure is applied. The load curve will show the rise in the load force that balances the blow-off force. The balanced fit produces a higher load than the retraction force of the headgear. The balanced fit component is the increasing force in the strap of the headgear that provides an equal and opposite force to the blow-off force. However, this force is also lower than the lengthening or extension curve. In some configurations, the slope of the balanced fit section is related to, influenced by, or can be substantially the same as the rise and/or the decline in the load force during retraction of the headgear. In some configurations, the slope of the balanced fit section is steeper than the slope in the decline in the load force. In some configurations, the slope of the balanced fit section is greater than the slope in the initial rise during lengthening of the headgear.

FIG. 42B shows the process of removing nasal seal module 101a, i.e., by gripping a lower part of mask frame 100 and pulling it away from the face of user U, while it remains strapped to the head, to naturally form a gap G, against the bias of an elastic portion of a headgear strap and by decoupling of the magnetic connection of the type described herein.

Still with reference to FIG. 42B the seal module 101a is then gripped at its accessible, bottommost, end and pulled toward the face of user U, thereby breaking the engagement between magnets 121a/121b and 122a/122b respectively. Nasal seal module 101a can then be decoupled from the posterior of the frame and removed through gap G between the user's face and mask frame 100. The force applied by the user U to achieve disengagement has to overcome the threshold forces that resist such disengagement. Disengagement can be achieved by 'peeling' the seal module away from the mask frame. By this process, the locator projection acts as a pivot whereby the seal module is pivoted upwardly about the locator projection to break the engagement between the magnets. Pivoting about the locator projection is facilitated by the wedge shape of the projection and that the height of the projection is less than the height if the locator recess.

With gap G still open a replacement seal module 101 can be inserted into the space in front of the face and connected to the rear side of the frame. The replacement seal module 101 may be the same type of seal module or a different type. For example, the replacement module may be a full face seal module where the original seal module is a nasal seal module. Mask frame 100 is then released to close gap G so that the replacement seal is brought into engagement with the user's face. Magnetic connections 121a/121b and 122a/122b respectively join frame 100 to the 'replacement' seal module 101, aided by locating features 121c/121d to correctly orient the components and the magnets themselves which will tend to pull the assembly into place by magnetic forces. In particular, wedge shaped locator 121c approaches locator recess 121d to guide mask frame 100 into position against seal module 101 before or at the same time as the corresponding magnets begin to engage by magnetic attraction.

In the illustrated form magnetic connections 121a to 121b etc. allows for the seal module 101/101a to be quickly and easily swapped out without the need to completely remove the full headgear or operate any complicated clipping means. Magnets being located at the lower part of the aperture with a locating feature at the top enables a seal module to be 'peeled' away by a relatively small force. Furthermore, magnets pull the parts into correct alignment, such that initial alignment does not need to be perfect between the rear/posterior of the mask frame and front/anterior of the seal module. The magnetic attachment system as described allows seal modules to be interchanged in the dark; e.g.

where a user may want to change between a full face and nasal mask during the night for comfort. It is intended that the conduit aperture is located in such a place that when the mask frame 100 is connected to either the nasal or full face module, the apex/bridge of the seal module will be in the same place relative to a user's facial geometry.

Magnetic Hold of Adjustment of Seal

FIGS. 10 and 11A-C show, and illustrate the operation of, a seal comprising at least one magnet or ferrous part associated with the seal to hold a first part of the seal in position relative to another part of the seal or part of the mask frame of the respiratory interface, to magnetically hold an adjustment position of a part of the seal. In the embodiment shown multiple magnets and/or ferrous parts are provided in a nasal bridge part 200 of the seal, to hold in the nasal bridge part of the seal in a selected adjustment position. The nasal bridge part 200 of the seal is compliant as indicated by arrow C in FIGS. 10, 11A and 11B, enabling the nasal bridge part of the soft flexible seal to move forward of its normal position shown in FIG. 11A, to for example either of the two positions shown in FIGS. 11B and 11C, to accommodate users with different depths of nasal bridge, so that the seal does not place excessive pressure on the nasal bridge area of the nose of the wearer. Such a compliant nasal bridge is described in our international patent publication WO2012/140514 the whole contents of which are incorporated herein by reference.

Figure 11A:
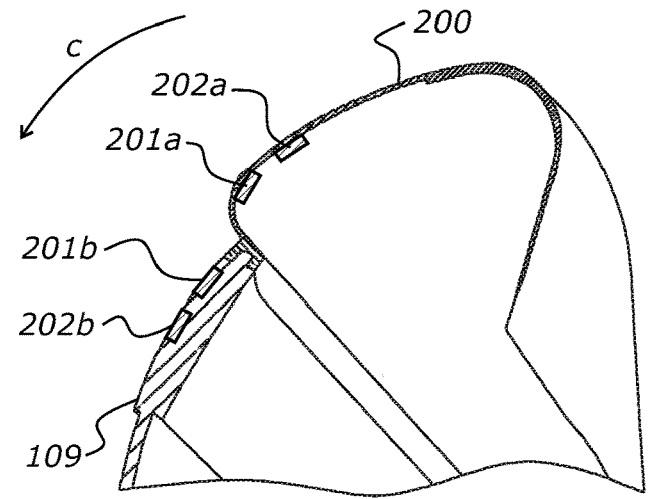
FIGS. 11A-C are cross-section views of the nasal bridge part the seal module of FIG. 10 along line I-I of FIG. 10 in different positions of adjustment of the nasal bridge part of the seal.
Figure 11B:
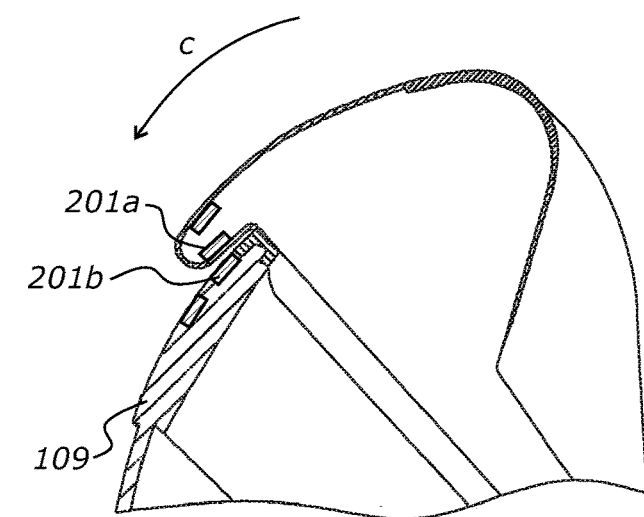
Figure 11C:
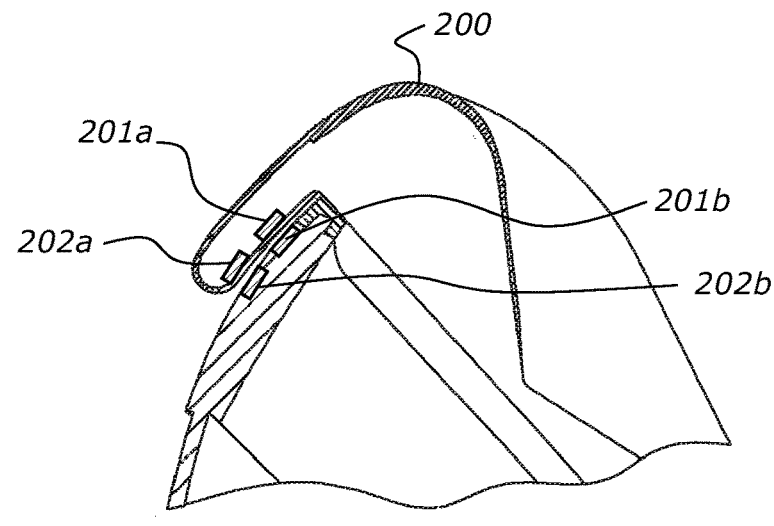
Figures 18, 19, 20:
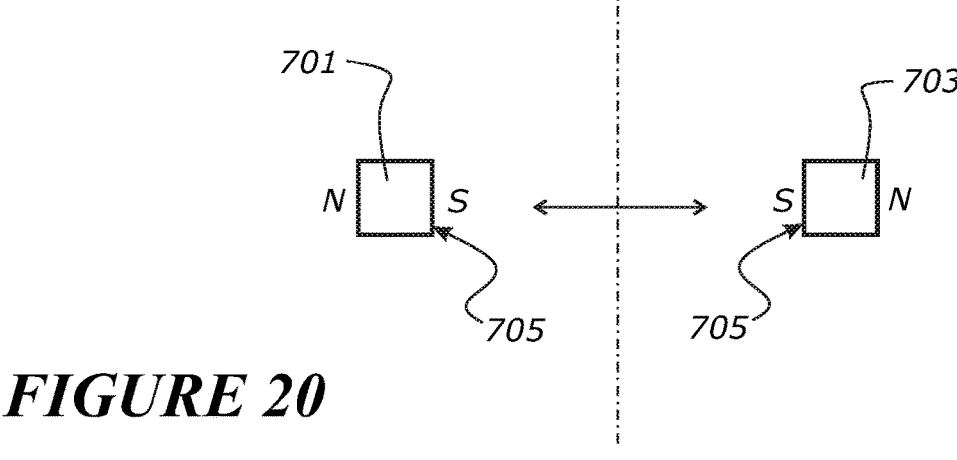
FIG. 18 is a schematic perspective view of a magnetic repulsing feature for a conduit.
FIG. 19 is a schematic top view of the magnetic repulsing feature of FIG. 18.
FIG. 20 is a schematic cross-sectional view of the magnetic repulsing feature of FIG. 18.
Figure 21:
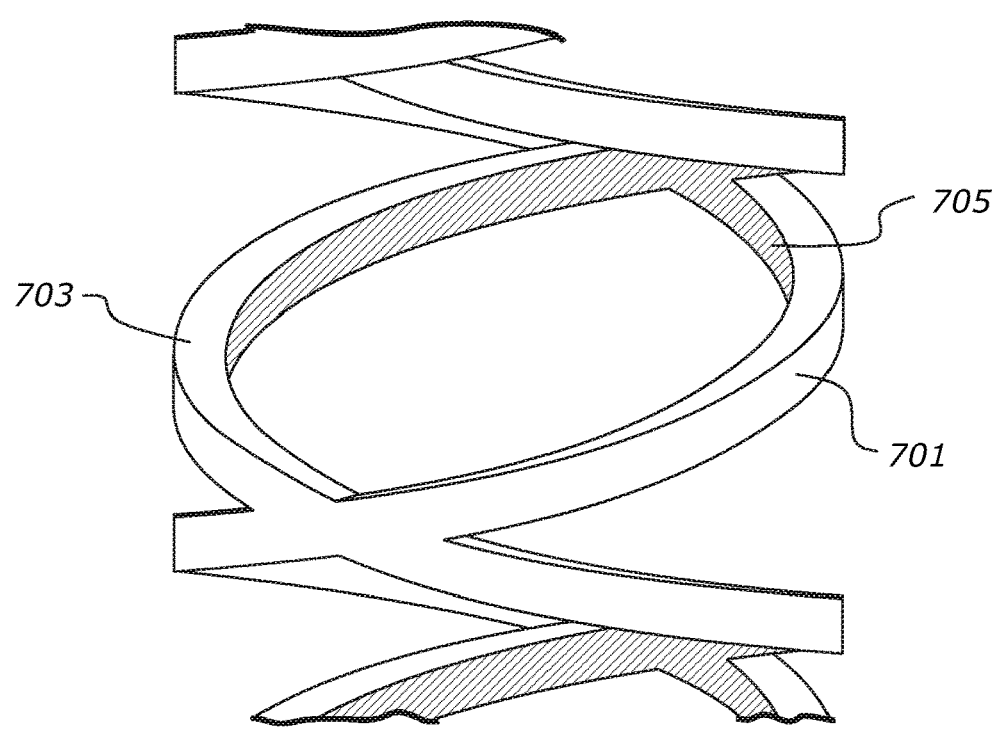
FIG. 21 is a schematic detailed perspective view of the magnetic repulsing feature of FIG. 18.

Magnets 201*a* and 202*a* are embedded in a forward part of the soft moulded material of the nasal bridge portion of the seal which moves to provide nasal bridge compliance of the seal, and magnets 201*b* and 202*b* are embedded in an adjacent (non-moving) part of the seal for example a shell part of the seal module formed of a relatively harder material (as escribed in relation to FIGS. 1 to 4 for example). The magnets particularly in the thin wall section flexing or folding nasal bridge part of the seal may comprise zones of embedded particulate material moulded in the silicone or other soft material from which the seal is formed, which extend transversely across the nasal bridge part of the seal from left to right for example (magnetic lines). The magnets are arranged with their poles oriented such that magnets will attract in defined discrete positions of adjustment. Two such positions are shown in FIGS. 11B and 11C. If the nasal bridge part of the seal is moved from the 'normal' position of FIG. 11A, to the position of FIG. 11B, to accommodate a medium depth nasal bridge user, in the position of FIG. 11B magnets 201*a* embedded in the nasal bridge portion of the seal and 201*b* embedded in the non-moving part of the seal, will align to hold the seal in this position of adjustment. However if the user pushes the nasal bridge part of the seal further forward, to the position shown in FIG. 11C, to accommodate a higher depth nasal bridge, a different pair of magnets namely magnets 202*a* embedded in the nasal bridge portion of the seal and 202*b* embedded in the non-moving part of the seal, will align also as shown, or instead, to hold this adjustment position.

The embodiment shown has two positions of magnetic hold of adjustment but in other embodiments magnets may be provided in the seal and/or frame to provide three or more, on only one, magnetic adjustment hold position.

In the embodiment shown the compliant nasal bridge is provided in the seal module of an interface comprising a mask frame and separate seal module but such a magnetic adjustment system of the nasal bridge may be provided in the compliant nasal bridge of a seal which is non-detachable from the mask frame for example a seal which is permanently overmoulded to the mask frame.

Nasal to Full Face Magnetically Connected Seal

FIG. 12 is a schematic side view of an embodiment of a respiratory interface comprising a nasal seal part and an oral seal part which are detachably magnetically coupled. The interface comprises an oral seal first part 300 to deliver gases through the mouth, supplied in the embodiment shown to the interface via conduit 301, and a nasal seal second part 302 to deliver gases to the nose also. The nasal seal part 301 may be an indirect or direct nasal seal as described. A magnetic coupling system magnetically couples the oral seal part 300 and nasal seal part 302 together to form, when coupled, a combined oro-nasal seal.

In the embodiment shown the oral seal part 300 comprises magnets 303 around an upper peripheral part and the nasal seal part comprises magnets 304 around a lower peripheral part, both on left and right sides and across the front of the seal, or alternatively a single strip magnet in each seal part instead of discrete magnets as shown, or embedded particulate magnetic material, embedded in the seal during moulding for example, which magnetically couple the seal parts together or embedded particulate magnetic material, embedded in a soft synthetic insert 350 during plastic moulding for example.

The seal parts may be attached to one another or coupled, and detached from one another, so that the interface may be used with both seal pats together or with the oral seal part only. In an alternative embodiment the conduit may connect to a nasal seal part so that an oral seal part may be magnetically coupled to or detached from the nasal seal part enabling the nasal seal part to be used alone.

In the embodiment shown the two seal parts 300 and 302 magnetically couple together but in an alternative embodiment one or both of the seal parts may also or alternatively magnetically couple to a common mask frame, again so that one or other of the seal parts may be detached to enable the interface to be used as an oral-only, or nasal-only, interface if the other seal part is detached.

In some embodiments the magnetic coupling system comprises at least one magnet associated with one of the first and second seal parts or mask frame and at least one ferrous part associated with one of the first and second seal parts or mask frame. In other embodiments the magnetic coupling system comprises magnets associated with each of the first and second seal parts or one of the first and second seal parts and the mask frame.

In some embodiments at least one magnet associated with one of the first or second seal parts or the mask frame and at least one magnet associated with another of the first or second seal parts or the mask frame are provided to the seal parts or mask frame such that they attract when the seal parts are coupled each other or to the mask frame in a predetermined correct orientation and repel in any orientation other than said predetermined correct orientation.

Magnetic Mouth Connection

FIG. 13 is a perspective view from above of an embodiment of an oral insert configured to be retained in a user's mouth when a mask is worn, to assist in retaining the mask in position on the face of the user. Oral insert 350 is configured to be retained at least in part on the teeth of the user. In the embodiment shown the oral insert 350 has an approximate U-shape as shown, and comprises an upwardly facing open channel 351, so that it is configured to be retained on the left right and front upper teeth of the user when worn. When worn the oral insert 350 remains attached to the teeth securely, but is shaped and sized so as to be as minimally invasive and as maximally comfortable as possible. The insert may be formed of a material which is soft but has some structural rigidity, such as a silicone material for example. The dimensions across the upwardly facing channel 351 are such that the insert will remain wedged on the teeth.

The insert comprises magnets 352 spaced around its forward periphery as shown, or alternatively a single magnetic strip may extend around the front periphery of the insert. The magnets or magnetic strip may comprise a solid magnet or magnets or embedded particulate magnetic material, embedded in a soft synthetic insert 350 during plastic moulding for example.

A corresponding magnet or magnets are provided on a mask (not shown in FIG. 13) particularly the seal or cushion at the left and right sides of in the upper lip region or across the upper lip region, so that when the oral insert 350 is in place on the user's teeth, and the mask is placed in the correct location on the face, the mask will magnetically couple to the oral insert 350 to at least assist in retaining the mask in position on the face of the user. This may be in addition to headgear coupled to the mask, so that the magnetic system stabilises the mask on the face for example, or in some embodiments the interface does not also comprise headgear and the magnetic coupling system through the oral insert 350 solely retains the mask in position when worn by the user.

In embodiments the magnetic coupling system comprises at least one magnet associated with one of the mask or oral insert and at least one ferrous part associated with the other of the mask or oral insert. In embodiments the magnetic coupling system comprises magnets associated with both of the mask or oral insert.

Magnetic Swivel

FIG. 14A is a longitudinal cross-section part view of a conduit connected to the end of an elbow of a mask by a magnetic coupling system according to an embodiment, and FIG. 14B is a longitudinal cross-section part view similar to FIG. 14A but in which only a part of the conduit is shown in cross-section. In these figures flexible conduit 400, for example from a CPAP machine to a respiratory interface, comprises at one end a rigid or semi-rigid annular part or fitting 401, which is received over a rigid or semi-rigid annular fitting 402 which is part of or attached to the interface. For example part 402 may be the lower end of an elbow connecting to the mask, or may be a fitting on the bottom end of a short lead in tube forming part of the mask. Annular magnets 403 are embedded in the part 401, for example during plastic moulding of the part 401, and corresponding annular magnets 404 are embedded in the part 402 during moulding of this part for example. There may be one or more magnets in each part, which may be discrete ring or segmented ring or magnets or embedded particulate magnetic material magnets. The magnets 403 and 404 are positioned, and part 401 has a slight internal taper and part 402 a slight external taper, so that when the parts 401 and 402 are brought together the magnets will align and magnetically couple part 401 on the end of conduit 400 to the part 402 on the bottom end of the elbow or mask lead in tube. The magnetic coupling may or may not form a frictionless or near frictionless swivel i.e. the part 401 can rotate about the longitudinal axis of the coupling without becoming detached from the part 402.

In the embodiment shown the magnet coupling system is between conduit 400 and part 402 which is described above as at the bottom end of an elbow or lead in tube to a mask but alternatively part 402 may be comprising a fitting such as a fitting of a CPAP machine for coupling a conduit to a CPAP machine or in any other context, or may be provided at the end of another length of conduit, for coupling together two conduit lengths, for example.

In embodiments the magnetic coupling system comprises at least one magnet associated with one of the conduit to the mask and the mask or a lead in tube to the mask and at least one ferrous part associated with another of the conduit to the mask and the mask or a lead in tube to the mask. In embodiments the magnetic coupling system comprises magnets associated with both of the conduit to the mask and the mask or a lead in tube to the mask.

In embodiments at least one magnet associated with one of the conduit to the mask and the mask or a lead in tube to the mask and at least one magnet associated with another of the conduit to the mask and the mask or a lead in tube to the mask are provided to the conduit and the mask or a lead in tube to the mask such that they attract when the conduit and the mask or a lead in tube to the mask are coupled each other or to the mask frame in a predetermined correct orientation and repel in any orientation other than said predetermined correct orientation.

Self-Centring

Figure 36:
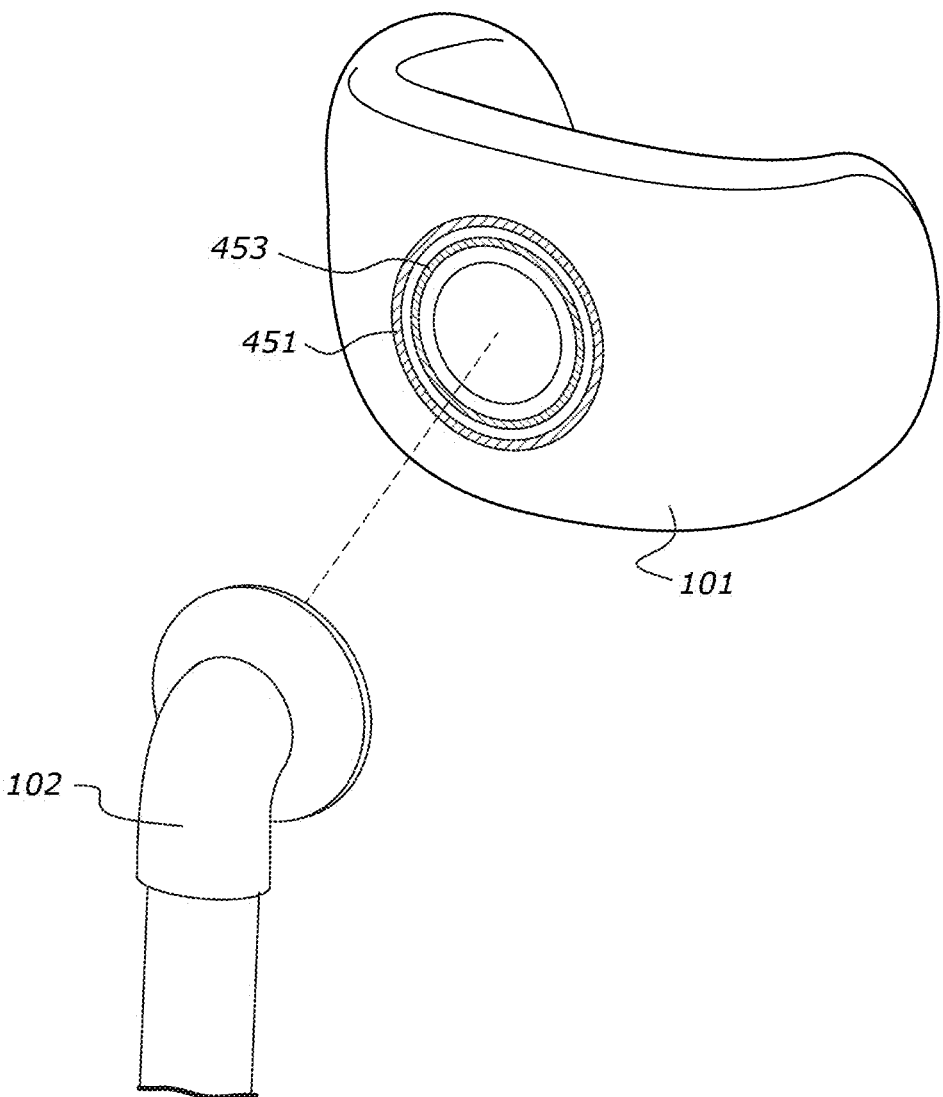
FIG. 36 is a schematic view of a seal module and elbow.

FIGS. 36 and 37 schematically show components of an embodiment of a respiratory interface having a magnetic coupling system 450 for connecting a conduit to a mask or to a lead in tube to the mask to deliver respiratory gases to the user. The illustrated components of the respiratory interface are a seal module 101 and elbow 102. The seal module 101 and elbow 102 may have the features and operation of earlier described embodiments, except the differences described below.

FIGS. 38a and 38b are schematic views of magnet parts of the seal module 101 and elbow 102 in incorrect and correct orientations relative to one another respectively. When the seal module 101 and the elbow 102 are correctly oriented (FIG. 38b), the outlet aperture 111 of the elbow and the inlet aperture 110 of the seal module are aligned. As shown in FIG. 38b this involves alignment of the apertures' 110, 111 central axis. FIG. 38a shows the misalignment of the apertures' 110, 111 central axis when the seal module and the elbow are incorrectly oriented.

The magnetic coupling system 450 comprises two annular magnets 451, 453 provided in the seal module 101 with a space between them. One magnet is a coupling magnet 453 and one magnet is a repulsing magnet 451. Both magnets 451, 453 surround and are spaced from the inlet aperture 110 of the seal module 101. The magnetic coupling system 450 also comprises an annular magnet 455 in the elbow 102 in a location such that it will align with the coupling magnet 453 on the seal module 101 when the elbow is correctly orientated with respect to the seal module. In the embodiment shown, the elbow 102 has a flexible flange 457 and the annular magnet 455 is provided at or near a periphery of the flexible flange 457. The flange 457 extends outwardly from the elbow 102 and extends around the perimeter of the elbow. Although it is to be appreciated that in other embodiments the flange only extends around a portion of the elbow or comprises a plurality of flange segments that are distributed about the perimeter of the elbow. The flange 457 is located close to the outlet aperture 111 of the elbow. The flange 457 is configured to be positioned over a portion of the seal module's external surface surrounding the inlet aperture 110. The flexibility of the flange enables the flange to conform to the shape of the seal module's external surface and form a seal.

Although in the illustrated embodiments of FIGS. 36-38 the magnets 451, 453, 455 are shown as unitary annular magnets, in other embodiments one or more of the magnets comprises two or more magnets in an annular arrangement. Any or all of the annular magnets 451, 453, 455 can be made from a soft magnetic material, such that it is conformable to the geometry of the seal module 101. A soft magnet may provide an airtight connection between the seal module 101 and the elbow 102.

The coupling magnet 453 in the seal module 101 has an opposite pole (for example north) to the magnet 455 of the elbow 102 (for example south). The repulsing magnet 451 will have the same pole as the magnet 455 of the elbow 102 (for example south). Thus, the seal module 101 and elbow 102 will attract only in one (correct) orientation and/or position of the seal module 101 relative to the elbow, as illustrated by FIG. 38a—incorrect orientation, and 38b—correct orientation. Further, when in the incorrect orientation, the magnets 451, 453, 455 will encourage the elbow 102 to move towards the correct orientation and/or position. This will occur if the elbow 102 is correctly aligned and is then moved or knocked. That is, the elbow 102 is self-centring or self-locating. If a user places the elbow 102 near the seal module 101, the magnets 451, 453, 455 will encourage the elbow 102 towards the correct orientation.

As described above in relation to other embodiments, interfaces of the invention may rely solely on magnetic attraction of the seal module 101 to the elbow 102. In alternative embodiments a magnetic coupling system supplements, and is provided in addition to, other coupling systems as described above. In some embodiments, the interface relies predominantly on mechanical coupling to hold the seal module 101 relative to the elbow 102, and a magnetic coupling system as described is provided primarily to self-centre the seal module 101.

Magnet Modular Headgear

FIG. 15 schematically shows an embodiment of headgear for a respiratory interface, comprising headgear parts and a magnetic coupling system arranged to magnetically couple headgear parts to one another.

In the embodiment shown the headgear comprises a rear strap 500 and top or crown strap 501, which couple magnetically to the ends of left and right side straps or side arms 503 from mask 504, which extend in use across the left and right sides of the face of the wearer. In the embodiment shown landing parts 503a are provided at the ends of side straps or arms 503. The left and right ends of rear strap 500 comprise a magnet or magnets and the left and right ends of top strap 501 each comprise a magnet or magnets, as do the landing parts 503a of left and right side straps or arms 503, so that the ends of the rear strap 500 and top strap 501 can be coupled to the ends 503a of the side straps or arms 503, to assemble the headgear for use as shown.

In embodiments the first and second, and optionally third or third and fourth headgear parts, comprise at least one magnet at or towards one end thereof and at least one ferrous part at or towards another end thereof.

The magnets may be discrete solid magnets or comprise embedded particulate magnetic material.

Headgear in any form such as bifurcated or four point headgear having both top and bottom side straps to the interface on left and right sides, may be formed in whole or part as described so that for example headgear may have a top strap which is attached to the rest of the headgear magnetically and can be removed if desired by the user.

In embodiments at least two magnets associated with one of one of the first and second, and optionally third or third and fourth headgear parts and another with another of the first and second, and optionally third or third and fourth headgear parts, are provided to the headgear parts such that they attract when the headgear parts are coupled in a predetermined correct orientation and repel in any orientation other than said predetermined correct orientation.

Headgear Buckle (Also Headgear to Mask Buckle)

FIGS. 16A and 16B show embodiments of headgear for a respiratory interface comprising a magnetic coupling system to magnetically couple headgear straps or parts together.

In FIG. 16A straps 540 and 542 adjustably connect together. Strap 540 carries protrusion 541 having a magnet or magnets associated therewith such as embedded in the strap at and within the protrusion during moulding of a plastic strap for example, or embedded in a separate plastic part in turn bonded to a strap of soft material strap such as Breath-O-Prene® or similar material strap for example. Strap 542 carries a series of adjacent apertures 543 each having a small annular magnet embedded in the strap around the aperture. The magnet in protrusion 541 and associated with apertures 543 are oriented such that when the protrusion 541 is entered into one of the apertures 543 it will magnetically attract to and couple to the strap.

FIG. 16B shows a similar embodiment in which protrusion 553 is provided on the underside of the end of strap 552, and recesses 551 which are optionally semi-connected to form a channel with corrugated sides as shown, are provided in the end of strap 550. Whereas in the embodiment of FIG. 16A the apertures 543 may penetrate completely through the strap end, in the embodiment of FIG. 16B the apertures 551 are blind and magnet or magnetic particulate material alternatively are embedded during plastic moulding of the strap for example in the base of the apertures 551. This embodiment also comprises a loop 554 through which the strap end 552 passes before connecting to strap 550.

Alternatively the magnetic protrusion 541 or 553 may be provided at or towards the end of a side strap which couples to a mask or forehead rest part of a mask, and apertures 543 or 551 provided on the left and right sides of the mask body or forehead rest, to couple the side straps to the mask body or forehead rest in the same way.

In embodiments the first headgear part comprises at least one magnet or at least one ferrous part associated with said protrusion and the second headgear part or mask comprises at least one magnet or at least one ferrous part associated with said one or more recesses. In embodiments the headgear comprises the first headgear part comprises at least one magnet associated with said protrusion and the second headgear part or mask comprises at least one magnet associated with said one or more recesses.

Headgear Connection Broken by 3rd Magnet

FIG. 17 shows an embodiment of headgear for a respiratory interface comprising a magnetic coupling system, and a decoupling tool.

In the embodiment shown magnet 600 is provided at or towards the end 601 of strap 602. For example magnet 600 may be a solid or particulate material magnet embedded within a plastic moulded strap end 600 of strap 602 which may otherwise be of a softer strap material for example. Magnet 603 is similarly embedded in another strap end or headgear part, or a mask body including forehead rest, for example. Decoupling tool 605 is provided, comprising solid or particulate material magnet 604 embedded therein. When the decoupling tool 605 is inserted between the strap ends or the strap and mask part, to decouple same, specifically in the example shown between magnet 600 and magnet 603, in the correct orientation, doing so will tend to force the strap ends or the strap and mask part, specifically in the example shown the magnets 600 and 603, apart decoupling the same. For example the decoupling tool 604 may be slid along the inside face of strap 602 and strap end 601 towards magnet 600 and 603 in use.

Preferably the decoupling tool 605 comprises a visual indicator on an exterior thereof indicating a correct orientation for inserting the decoupling tool 605 between the straps and mask or two straps. For example the decoupling tool may have a colour or word or shape embedded in or marked on the surface of one or both sides, such as 'inside' and 'outside' or similar, or the decoupling tool may be formed in a shape which indicates to a user the correct orientation relative to the parts being decoupled in which the tool should be used. In a further embodiment the decoupling tool 605 may have a tapered/sharp leading edge in order to initially prise apart coupled magnets, with decoupling of magnets 600 and 603 further assisted by an embedded magnet 604 as the tool is manually pushed therebetween.

With reference to FIGS. 27 to 29, another embodiment of headgear for a respiratory interface is shown. The interface may have the features and operation of earlier described embodiments, except the differences described below. The headgear comprises a first headgear part having an inflatable portion, a second headgear part, a magnetic coupling system arranged to magnetically hold the first and second headgear parts together. The first headgear part and second headgear part are left and right side arms 503 respectively. The arms 503 are in the form of straps. The first left and right side arms 503 overlap when engaged.

FIG. 28*a* shows a cross-section of an arm 503 that is free of magnetic material. FIG. 28*b* having a magnet 561. The left and right side arms 503 both comprise magnet free portions and portions with one or more magnets 561. As described in relation to other embodiments, each magnet 561 may be a solid or particulate material magnet embedded within a plastic moulded strap end of the strap which may otherwise be of a softer strap material for example.

The headgear has a decoupling mechanism that moves the arms and decouples the magnets. The decoupling mechanism comprises a pump associated with the inflatable portion that is arranged such that activation of the pump causes the inflatable portion to inflate, causing the first and second parts to move relative to each other. The pump is a squeeze pump that causes the inflatable portion to inflate by being squeezed by a user. The pump is preferably formed as part of the mask 504, but may be provided as part of the arms 503 or other part of the interface or headgear.

In the embodiment shown, the left and right side arms 503 both have an inflatable portion and activation of the pump causes the inflatable portion of both arms to inflate. The arms 503 move away from each other by one or both of the arms moving from a curved configuration (FIG. 29) to a relatively straight configuration (FIG. 27). In the embodiment shown, a substantial portion or the entire length of each or both of the arms 503 is inflatable. As shown in FIGS. 28*a* and 28*b* the inflatable portion of the arm(s) is provided by a hollow core 505 formed in the arms.

Figures 30, 31, 32:
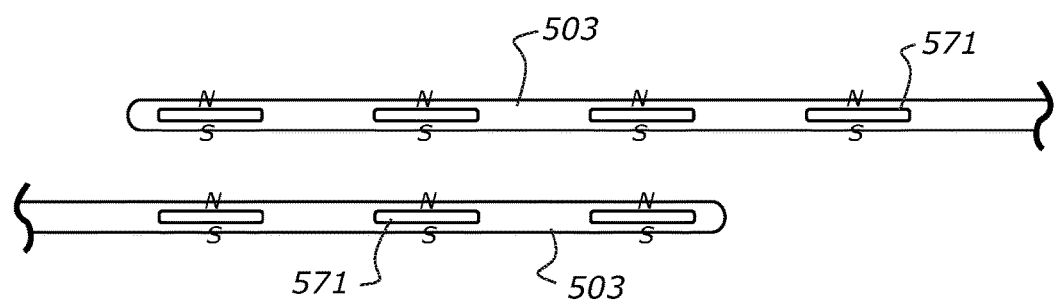
FIG. 31 is a schematic view of the headgear of FIG. 30 in a relatively large sized, in-use configuration.
FIG. 32 is a schematic view of the headgear of FIG. 30 in a relatively small sized, in-use configuration, FIG. 33 schematically shows another embodiment of headgear for a respiratory interface, comprising headgear parts and a magnetic coupling system arranged to magnetically couple headgear parts to one another.

With reference to FIGS. 30 to 32, another embodiment of headgear for a respiratory interface is shown. The interface may have the features and operation of earlier described embodiments, except the differences described below. In FIGS. 31 and 32, the arms 503 adjustably connect together. Both straps have magnets 571 associated therewith such as embedded in the arms 503 during moulding of a plastic strap for example, or embedded in a separate plastic part in turn bonded to a strap of soft material strap such as Breath-O-Prene® or similar material strap for example. The magnets 571 in each arm 503 are oriented such that when the straps overlap, they will magnetically attract to each other. In alternative embodiments, one of the arms 503 has magnets and the other strap has at least one ferrous portion. FIG. 31 is a schematic view of the headgear of FIG. 30 in a relatively large sized configuration, and FIG. 32 is a schematic view of the headgear of FIG. 30 in a relatively small sized, in-use configuration.

Figure 33:
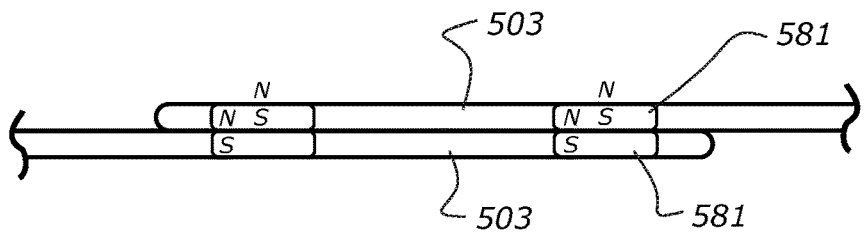
Figure 34:
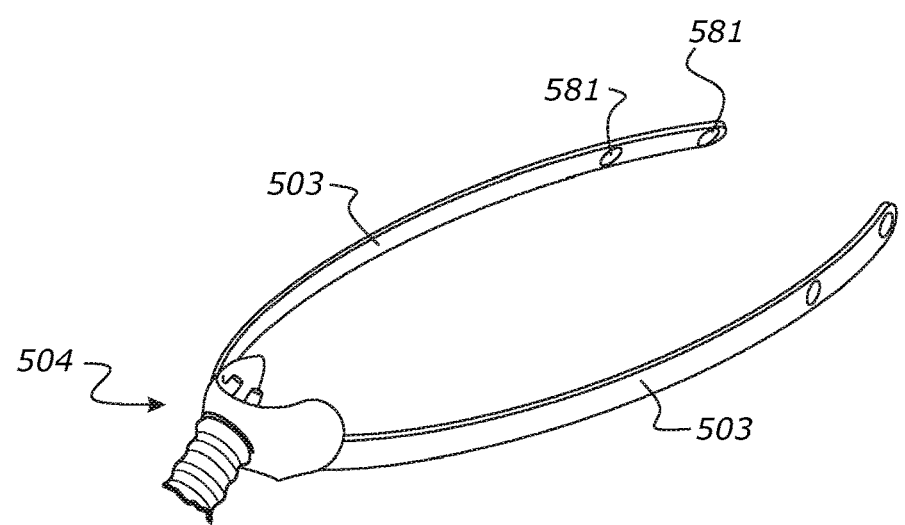
FIG. 34 is a schematic view of the headgear of FIG. 33 in an open configuration.
Figure 35:
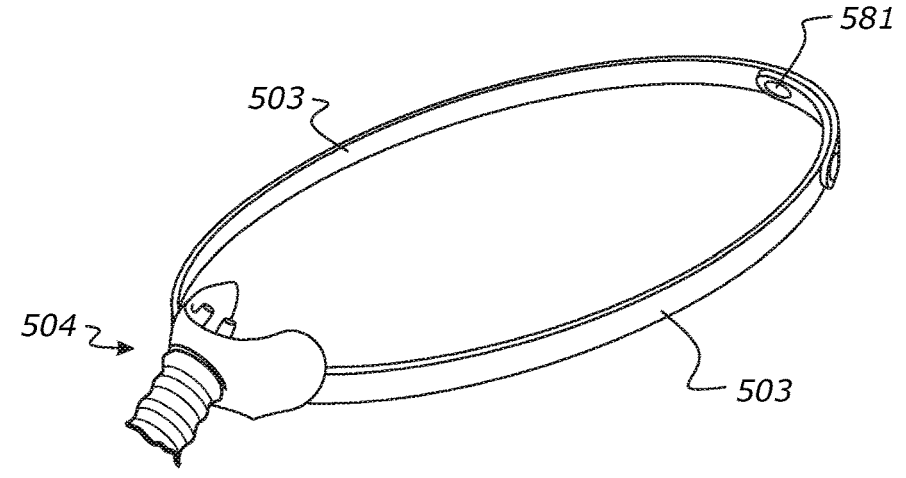
FIG. 35 is a schematic view of the headgear of FIG. 33 in a closed configuration.

With reference to FIGS. 33 to 35, another embodiment of headgear for a respiratory interface is shown. This embodiment is similar to the embodiment shown and described in relation to FIGS. 30 to 32, except that the size of the strap is personalised to the user. In particular, the user's head will be measured and the straps will be manufactured to have the magnets 581 positioned in the correct location to fit the user.

Further Disclosure Regarding Headgear

In some configurations, portions of the headgear assembly can be substantially non-stretchable. For example, the back strap, top strap and upright straps can be non-stretchable such that the portion that encircles the occipital region of the users head is made from non-stretch material. In some configurations, non-stretchable portions can comprise of a substantially non-stretch insert. The non-stretch insert can be attached to the headgear assembly, for example, by over-lock stitching, by ultrasonic welding, by use of glue or other adhesives, or by any other method. In some configurations, one or more of the side straps can also be formed of a substantially inelastic or non-stretchable material. The side straps can be formed of a semi-rigid, self-supporting material such that the semi-rigid headgear assembly can assume a substantially three-dimensional shape and generally does not tangle. The non-stretchable characteristic can be achieved by embedding at least one relatively inelastic panel in the portion of the headgear assembly that is desirably non-stretchable. The panel can be formed of a relatively low-stretch material, such as a polyester Breath-O-Prene® material, for example but without limitation. In some configurations, the headgear can be semi-rigid to secure the mask assembly to the user's head. The semi-rigid headgear can be formed as a composite structure comprising a semi-rigid strap that is joined to a soft edging. For example, the soft edging can be bonded to the semi-rigid strap by plastic overmolding or by use of an adhesive. The soft edging can be butt-joined to the semi-rigid strap, without the soft edging overlapping the semi-rigid strap, to maintain the continuous profile of the semi-rigid headgear. The semi-rigid strap can define and maintain the semi-rigid headgear shape as tension is applied from the straps to pull the mask assembly towards the user's head. In other words, the semi-rigid strap can be sufficiently rigid along its planar axis to prevent its upper and lower side straps from overly deforming under tension. The semi-rigid strap can be made from a variety of rigid or semi-rigid materials, including plastic or metal. In some configurations, the semi-rigid strap is made from PVC. Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form as discussed earlier, the headgear can be fitted in the correct orientation with very little if any instruction. In a self-supporting arrangement, the tendency of the straps to not tangle also reduces the time taken to fit the overall assembly. As used herein, the term "semi-rigid" is used to denote that the headgear assembly is sufficiently stiff such that the headgear assembly can assume a three-dimensional shape with dimensions approximating the head of the user for which the headgear is designed to fit while also being sufficiently flexible to generally conform to the anatomy of the user. For example, some of the other components (e.g., side straps) of the headgear assembly may also be partially or wholly "semi-rigid" such that the components are capable of holding a three-dimensional form that is substantially self-supporting. A "semi-rigid" headgear assembly is not intended to mean that each and every component of the headgear assembly is necessarily semi-rigid. For example, the substantially three-dimensional form that the self-supporting headgear assembly may assume may relate primarily to the rear and top portions of the headgear assembly. In addition, the semi-rigid headgear assembly may include semi-rigid regions that extend forward of the ears and above the ears when placed on the head of the patient.

The upper and lower side straps can be formed of a semi-rigid material, as well. Where used herein, the semi-rigid materials can include molded plastic or sheet materials that include, but are not limited to, homogeneous plastic materials and bonded non-woven fiber materials. In some configurations, the semi-rigid properties of the materials can be achieved with high-density foam material. The dense foam material can provide some structural rigidity to the upper and lower side straps, or other portions of the headgear assembly. In some configurations, the semi-rigid material can include textiles that are semi-rigid, such as denim or hemp. In some configurations, the material can comprise a laminate structure of both conformable and semi-rigid portions, for example but without limitation. The semi-rigid straps may be of a self-supporting, resilient, substantially inelastic material, such as Santoprene, polyolefin, polypropylene, polyethylene, foamed polyolefin, nylon or non-woven polymer material for example but without limitation. In some configurations, the semi-rigid strap is formed from the polyethylene or polypropylene families. The semi-rigid strap can be formed of a material such that the semi-rigid headgear is substantially shape-sustaining under its own weight regardless of its orientation. A soft edging can cover or attach to at least a portion of the periphery of the semi-rigid strap. In some configurations, the soft edging does not cover the front or rear faces of the semi-rigid strap and is instead attached adjacent to the edge of the semi-rigid strap. For example, the thicknesses of the soft edging and semi-rigid strap can be the same at the location where they are joined together. As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially "non-stretchable." The soft edging can have a uniform thickness, or in some configurations, an uneven thickness. For example, in some configurations the soft edging is the same thickness as the semi-rigid strap. In other configurations, the soft edging is thinner than the semi-rigid strap, forms a bulbous end to the semi-rigid strap, or is simply thicker than the semi-rigid strap. Any one particular soft edging thickness and shape can apply to a portion or the entire semi-rigid strap, or may be combined with any other particular covering thickness and shape. Many other thickness configurations may be provided, as well. In addition, material thickness may be symmetrically or asymmetrically applied to the semi-rigid strap. For example, in some configurations the thickness of either end the soft edging is symmetrically applied to the semi-rigid strap. In some configurations the semi-rigid strap is selectively thickened to provide extra rigidity and support. Finally, in some configurations, venting through-holes are provided throughout the semi-rigid headgear (such as on the semi-rigid strap or on soft edging) to provide ventilation and sweat management.

With reference to FIGS. 18 to 22, a magnetic repulsing system is shown that is adapted to be incorporated into a conduit for delivering respiratory gases to a user. The conduit is connectable to a mask or to a lead in tube to the mask and comprises an inlet, an outlet, and an enclosing wall defining at least one gases passageway between said inlet and said outlet. The magnetic repulsing system is incorporated into the enclosing wall to magnetically repulse a portion of the wall from a diametrically opposite portion of the wall. In particular, the magnetic repulsing system comprises one or more magnets that are spiral or helically shaped magnets. The embodiment of FIGS. 18 to 22 has two spiral or helically shaped magnets of which one spirals in a clockwise direction 701 and the other spirals in a counter-clockwise direction 703. In an alternative embodiment, the magnetic repulsing system comprises a single spiral or helically shaped magnet. The inner surfaces 705 of the magnets that face each other are the same pole and repel each other. As a consequence, the repulsion prevents or at least substantially inhibits the conduit from being crushed or compressed.

With reference to FIGS. 23 to 26, a magnetic system according to another embodiment that is adapted to be incorporated into a conduit for delivering respiratory gases to a user, is shown. The magnetic system is arranged to magnetically collect, i.e. automatically retract and/or retain, a portion of a length of an enclosing wall of the conduit. In particular, the adjacent surfaces 805 of the magnets are the opposite poles and attract each other. As a consequence, the magnet collects a length of the conduit into a shorter length. The conduit may stretch, fold, or gather between the longer and shorter lengths. As the conduit, or a portion of the conduit, is stretched or pulled, the adjacent magnet portions will initially work against the pulling force and maintain the conduit in the shorter length. However, as the pulling force is increased, the magnetic force will be overcome and the conduit, or portion of the conduit, will have the longer length. FIG. 24 shows a portion of conduit in which the lower portion is collected by the magnetic coupling system and the upper portion is configured such that the adjacent magnetic portions are spaced at a distance that is greater than their fields reach so the conduit is not collected.

Figure 22:
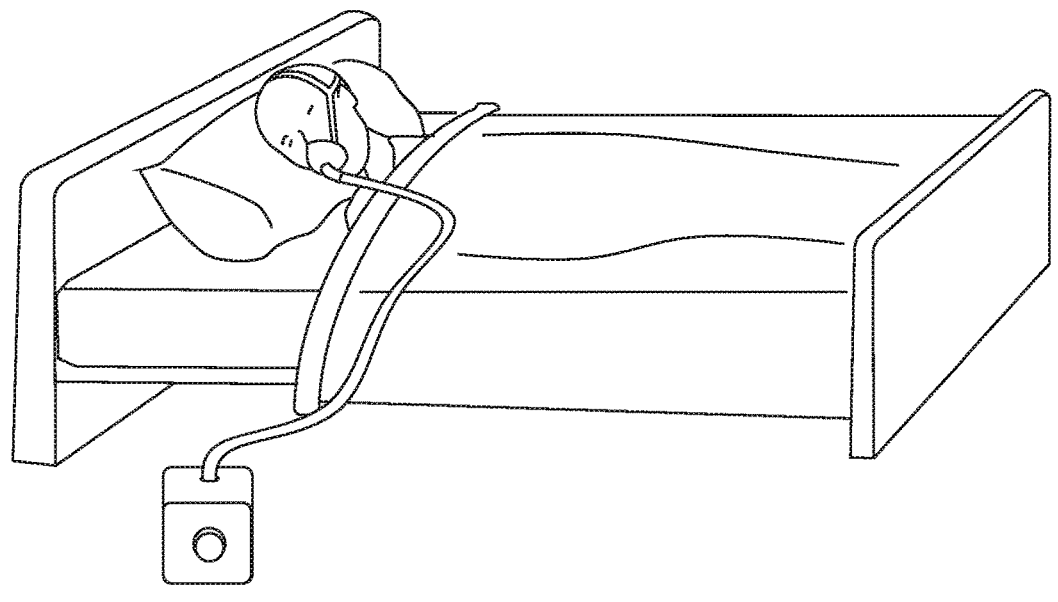
FIG. 22 is a schematic view of a respiratory interface comprising a conduit incorporating the magnetic repulsing feature of FIG. 18.

For the embodiments described above in relation to FIGS. 18 to 26, the magnets may comprise a segment of solid (non-particulate) magnetic material or may comprise particulate magnetic material. The particulate magnetic is material embedded in a part of the conduit. For example, the particulate magnetic material may be integrally formed with the enclosed wall, such as during an extrusion process. The magnets may extend along part of, substantially most of, or the entire length of the conduit. In addition, the magnets may extend around only part of the circumference of the conduit. The enclosing wall is preferably a soft and flexible material. The soft and flexible material is comfortable against the wearer's face, such as a silicone material. Furthermore, the magnets are preferably formed from soft magnetic material and thus provide the conduit with a soft and flexible feel for the patient. The material may also provide a grip to anchor or secure the hose to adjacent objects, such as a bed cover (FIG. 22).

The foregoing describes the invention including preferred forms thereof and alterations and modifications as will be obvious to one skilled in the art are intended to be incorporated in the scope hereof.

The invention claimed is:

1. A respiratory interface comprising:
a mask frame,
a seal module that couples to the mask frame and that is configured to interface to a mouth and/or nose of a user to deliver respiratory gases to the user, and
a magnetic coupling system that magnetically couples the seal module to the mask frame,
wherein the magnetic coupling system comprises at least one magnet associated with one of the seal module or the mask frame and at least one other magnet or ferrous part associated with an other of the seal module or the mask frame that are attracted to one another by a magnetic attraction force,
wherein one or both of the at least one magnet and the at least one other magnet or the ferrous part is elastically moveably mounted by an elastically movable mount comprising a stretchable material and configured such that when the seal module and the mask frame are brought towards one another, at a break point at which the magnetic attraction force exceeds an elastic retractive force of the elastic elastically movable mount, one or both of the at least one magnet and the at least one other magnet or the ferrous part moves within and relative to a balance of a respective one of the seal module and the mask frame in a manner that stretches the elastically movable mount before the elastically movable mount recovers as the seal module and the mask frame are fully coupled,
wherein an audible sound is produced on coupling and uncoupling of the magnetic coupling system,
wherein, on coupling of the magnetic coupling system, the at least one magnet or the at least one other magnet or the ferrous part moves relative to the balance of the seal module or the mask frame in response to the magnetic attraction force and the audible sound is produced by direct or indirect physical contact between the at least one magnet and the at least one other magnet or ferrous part, which contact stops the movement of the at least one magnet or the at least one other magnet or the ferrous part,
wherein, on uncoupling of the magnetic coupling system, the at least one magnet or the at least one other magnet or the ferrous part moves relative to the balance of the seal module or the mask frame in response to the elastic retractive force and the audible sound is produced by direct or indirect physical contact between the at least one magnet or the at least one other magnet or ferrous part and the seal module or the mask frame, which contact stops the movement of the at least one magnet or the at least one other magnet or the ferrous part, and
wherein the audible sound is produced only by the at least one magnet or the at least one other magnet or the ferrous part directly or indirectly audibly striking one another or one of the seal module or the mask frame.

2. The respiratory interface according to claim 1, wherein the at least one magnet or the at least one other magnet comprises a segment of solid magnetic material.

3. The respiratory interface according to claim 1, wherein the at least one magnet or the at least one other magnet comprises particulate magnetic material embedded in the seal module or the mask frame.

4. The respiratory interface according to claim 1, wherein the at least one magnet or the at least one other magnet or the ferrous part associated with the seal module are provided at or around an aperture into the seal module which interfaces with the mask frame to receive a flow of respiratory gases through the aperture into the seal module.

5. The respiratory interface according to claim 4, further comprising a gel material captured around the aperture into the seal module or an aperture through the mask frame.

6. The respiratory interface according to claim 1, wherein the at least one magnet or the at least one other magnet or the ferrous part associated with the mask frame are provided at or around an aperture through the mask frame which interfaces with the seal module to deliver a flow of respiratory gases through the aperture into the seal module.

7. The respiratory interface according to claim 1, wherein the mask frame and the seal module each include a mating locating feature, the mating locating feature comprising interfacing structures that are configured to limit relative rotation therebetween.

8. The respiratory interface according to claim 7, wherein the mating locating feature is at an upper part of the mask frame and the seal module respectively.

9. The respiratory interface according to claim 7, wherein the seal module is a first seal module and the respiratory interface comprises a second seal module with a second mating locating feature similar to the mating locating feature of the first seal module, wherein the first seal module and the second seal module are interchangeable and are each configured to couple to the mask frame.

10. The respiratory interface according to claim 9, wherein the second seal module is configured to interface to a different part of a face of the user than the first seal module.

11. A method of attaching the second seal module for the respiratory interface according to claim 9, wherein the mask frame, the first seal module and a headgear is in place upon a user, including the steps of:
moving the mask frame away from the user to open a gap between the mask frame and an airway of the user,
moving the first seal module toward the user, thereby breaking a magnetic coupling between the mask frame and the first seal module,
removing the first seal module through the gap,
inserting the second seal module through the gap,
positioning the second seal module over at least one airway of the user, and
returning the mask frame toward the user to close the gap and engage the magnetic coupling system.

12. The method of claim 11, further comprising moving the mask frame away from the user against a biasing element of a strap of the headgear.

13. The method of claim 12, wherein the biasing element is an elastic portion of the strap.

14. The method of claim 13, wherein the mask frame remains engaged at a forehead portion of the headgear and the mask frame is pulled away from the user at a lower portion of the user, thereby creating or widening the gap at a mouth region of the user.

15. The method of claim 11, further comprising moving the mask frame away from the user, thereby decoupling a magnetic coupling between the mask frame and the headgear.

16. The method of claim 11, wherein the moving the first seal module toward the user comprises pivoting the first seal module about a structure of the mask frame spaced apart from the magnetic coupling system.

17. The method of claim 16, wherein the structure is a locator projection that is received within a locator recess of the first seal module.

18. The respiratory interface according to claim 1, wherein the at least one magnet or the at least one other magnet or the ferrous part is located at a lower portion of the mask frame or the seal module.

19. The respiratory interface according to claim 18, wherein the at least one magnet and the at least one other magnet or the ferrous part are located on opposite sides of an opening through the mask frame or the seal module or both.

20. The respiratory interface according to claim 1, wherein the stretchable material is a soft synthetic elastic material and the at least one magnet or the at least one other magnet or the ferrous part are embedded in the soft synthetic elastic material.

21. The respiratory interface according to claim 1, wherein the at least one magnet or the at least one other magnet or the ferrous part are captured on a rim of the seal module by an elastically stretchable fabric cover that comprises the stretchable material and forms the elastically movable mount.

22. The respiratory interface according to claim 1, wherein the at least one magnet is associated with the seal module, and wherein the magnetic coupling system comprises the at least one other magnet or the ferrous part and the at least one other magnet or ferrous part is associated with the mask frame.

23. The respiratory interface according to claim 1, wherein the at least one magnet and the at least one other magnet or the ferrous part associated with the seal module and the mask frame are provided to the seal module and the mask frame such that the at least one magnet and the at least one other magnet or the ferrous part attract when the seal module is coupled to the mask frame in a single predetermined orientation of the seal module relative to the mask frame and repel when the seal module is offered to the mask frame in any orientation other than the single predetermined orientation.

* * * * *